(12) United States Patent
Tahara et al.

(10) Patent No.: US 10,448,916 B2
(45) Date of Patent: Oct. 22, 2019

(54) X-RAY CT SYSTEM

(71) Applicant: Toshiba Medical Systems Corporation, Otawara (JP)

(72) Inventors: Hiroto Tahara, Otawara (JP); Masayuki Wakahara, Utsunomiya (JP)

(73) Assignee: Canon Medical Systems Corporation, Otawara-shi (JP)

( * ) Notice: Subject to any disclaimer, the term of this patent is extended or adjusted under 35 U.S.C. 154(b) by 255 days.

(21) Appl. No.: 15/496,415

(22) Filed: Apr. 25, 2017

(65) Prior Publication Data
US 2017/0303870 A1    Oct. 26, 2017

(30) Foreign Application Priority Data

Apr. 26, 2016  (JP) .................................. 2016-088034
Mar. 28, 2017  (JP) .................................. 2017-062961

(51) Int. Cl.
*A61B 6/00* (2006.01)
*A61B 6/04* (2006.01)
*A61B 6/03* (2006.01)

(52) U.S. Cl.
CPC .............. *A61B 6/547* (2013.01); *A61B 6/032* (2013.01); *A61B 6/0407* (2013.01); *A61B 6/0457* (2013.01); *A61B 6/4417* (2013.01); *A61B 6/4441* (2013.01); *A61B 6/465* (2013.01); *A61B 6/504* (2013.01); *A61B 6/5205* (2013.01); *A61B 6/588* (2013.01)

(58) Field of Classification Search
CPC ......... A61B 6/547; A61B 6/032; A61B 6/035; A61B 6/0407; A61B 6/0457; A61B 6/4417; A61B 6/4441; A61B 6/465; A61B 6/504; A61B 6/5205; A61B 6/588

USPC .......................................... 378/4–20, 62, 63
See application file for complete search history.

(56) References Cited

U.S. PATENT DOCUMENTS

| | | | | |
|---|---|---|---|---|
| 2001/0007588 A1* | 7/2001 | Iizuka | ...................... | A61B 6/04 378/209 |
| 2002/0039403 A1* | 4/2002 | Oota | ...................... | A61B 6/032 378/196 |
| 2008/0281181 A1* | 11/2008 | Manzione | .............. | A61B 6/032 600/407 |

FOREIGN PATENT DOCUMENTS

| | | |
|---|---|---|
| JP | 7-382 | 1/1995 |
| JP | 2001-190535 | 7/2001 |
| JP | 2002-143142 | 5/2002 |
| JP | 5085219 | 11/2012 |

* cited by examiner

*Primary Examiner* — Courtney D Thomas
(74) *Attorney, Agent, or Firm* — Oblon, McClelland, Maier & Neustadt, L.L.P.

(57) ABSTRACT

According to an embodiment, an X-ray CT system includes a gantry, a first couch, a second couch, a carrier unit, and control circuitry. The gantry includes an X-ray tube, an X-ray detector, and an operation unit. The first couch is arranged in a first room. The second couch is arranged in a second room. When carrying the gantry to the first room, the carrier unit arranges the gantry in an orientation in which the front side of the gantry faces the first couch. When carrying the gantry to the second room, the carrier unit arranges the gantry in an orientation in which the back side of the gantry faces the second couch. The control circuitry controls the direction of the tilt movement of the gantry in accordance with the room where the gantry is arranged.

18 Claims, 18 Drawing Sheets

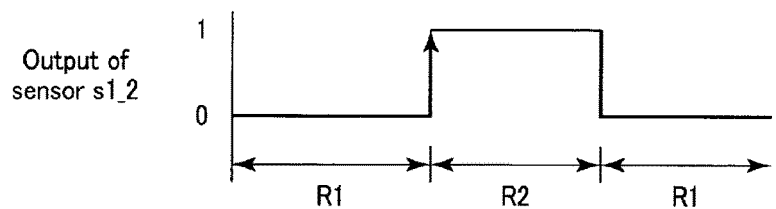

FIG. 6

| Sensor information (s1_2) | Combination | | Examination room | Control information |
|---|---|---|---|---|
| | Orientation of gantry (with respect to couch) | Couch | | |
| 0 | Front side | CT couch | R1 | Couch top slide control: reference direction<br>Tilt movement control: reference direction |
| 1 | Back side | Angio couch | R2 | Self-propelled gantry control: opposite direction<br>Tilt movement control: opposite direction |

FIG. 7

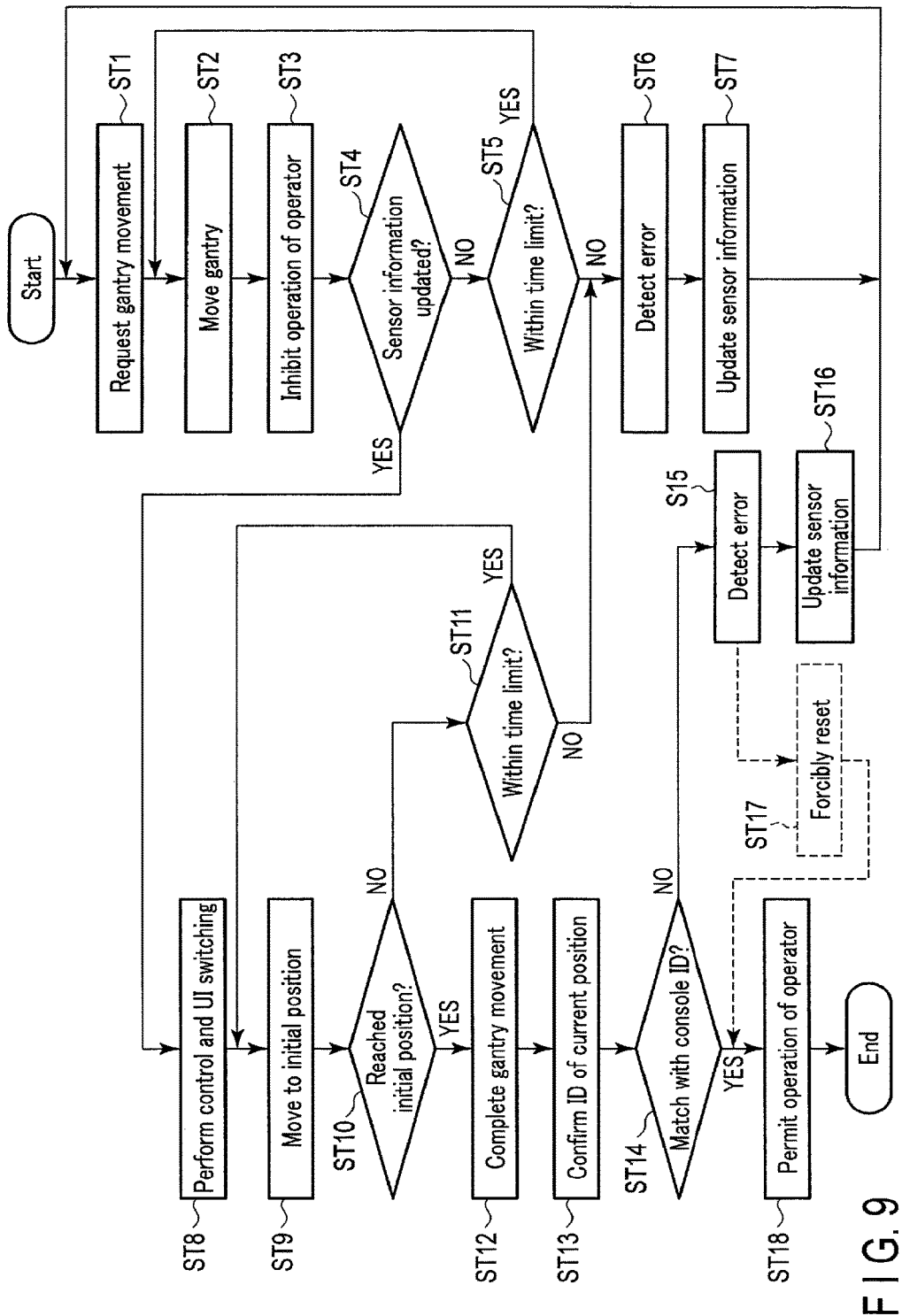
F I G. 9

| Sensor information (s1_2~s4_1) | Combination | | Examination room | Control information |
|---|---|---|---|---|
| | Orientation of gantry (with respect to couch) | Couch | | |
| 0x0 | Front side | CT couch | A | Couch top slide control: reference direction<br>Tilt movement control: reference direction |
| 0x1 | Front side | Angio couch | B | Self-propelled gantry control: reference direction<br>Tilt movement control: reference direction |
| 0x3 | Back side | CT couch | C | Couch top slide control: opposite direction<br>Tilt movement control: opposite direction |
| 0x7 | Back side | Angio couch | D | Self-propelled gantry control: opposite direction<br>Tilt movement control: opposite direction |

FIG. 13

X-RAY CT SYSTEM

CROSS-REFERENCE TO RELATED APPLICATIONS

This application is based upon and claims the benefit of priority from prior Japanese Patent Applications No. 2016-088034, filed on Apr. 26, 2016, and No. 2017-062961, filed on Mar. 28, 2017, the entire contents of all of which are incorporated herein by reference.

FIELD

Embodiments described herein relate generally to an X-ray CT system.

BACKGROUND

An X-ray CT (Computed Tomography) apparatus and an angio-CT apparatus are placed in one examination room as one system. The X-ray CT apparatus includes a gantry (CT gantry), a couch, and a console. The angio-CT apparatus includes a C-arm, a gantry (CT gantry), a couch, and a console. In a system of this type, the availability factor of the gantry of the angio-CT apparatus is low and is required to be improved.

On the other hand, as a system for improving the availability factor of a gantry by causing a plurality of examination rooms, that is, a plurality of systems to share a gantry, a multi-room solution is known in which a gantry moves among examination rooms.

Usually, this system does not particularly have a problem. However, according to the examination of the present inventor, when the gantry is shared, the positional relationship to the couch of each system or the combination of the systems change. This causes a mismatch in movement control of the gantry or user interface (to be referred to as a UI hereinafter) display on the operation panel or console. As a result, an operation error readily occurs in an operation unit serving as a UI.

The object is to provide an X-ray CT system capable of preventing an operation error in the operation unit of a gantry.

BRIEF DESCRIPTION OF THE DRAWINGS

FIG. 6 is a schematic view showing a sensor output according to the embodiment;

FIG. 7 is a schematic view showing contents stored in a memory according to the embodiment;

FIG. 9 is a flowchart for explaining an operation according to the embodiment;

FIG. 13 is a schematic view showing contents stored in a memory according to the embodiment;

DETAILED DESCRIPTION

Figure 1:
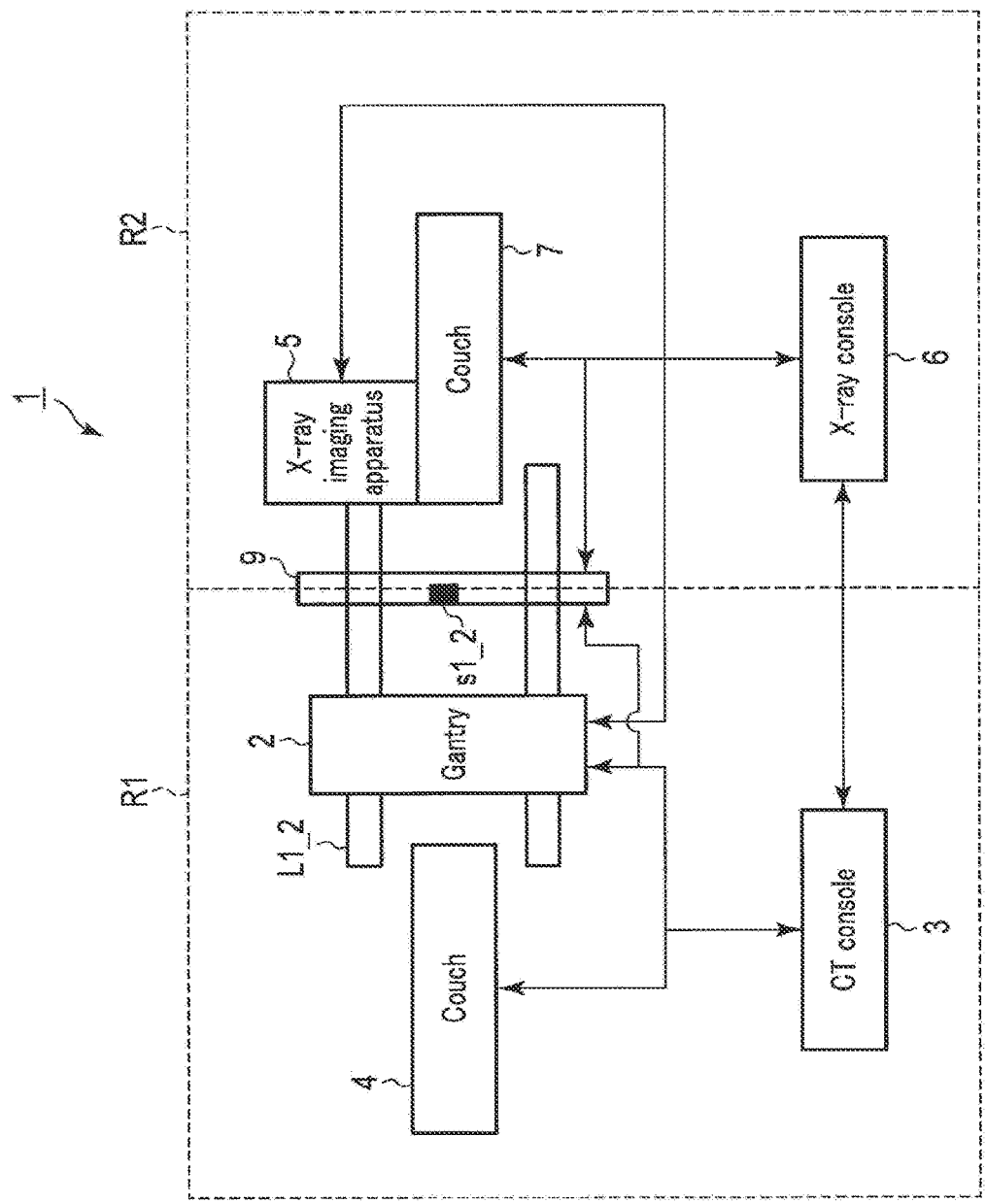
FIG. 1 is a block diagram showing the arrangement of an X-ray CT system according to the first embodiment.

According to an embodiment, an X-ray CT system includes a gantry, a first couch, a second couch, a carrier unit, and control circuitry.

The gantry includes an X-ray tube, an X-ray detector configured to detect X-rays emitted by the X-ray tube, and an operation unit configured to generate a command signal to command a tilt movement in accordance with an operation of an operator.

The first couch is arranged in a first room. The second couch is arranged in a second room.

The carrier unit includes a motor. When carrying the gantry to the first room, the carrier unit arranges the gantry in an orientation in which the front side of the gantry faces the first couch. When carrying the gantry to the second room, the carrier unit arranges the gantry in an orientation in which the back side of the gantry faces the second couch.

During the generation of the command signal by the operation unit, the control circuitry controls the direction of the tilt movement of the gantry in accordance with the room where the gantry is arranged.

The X-ray CT system according to an embodiment will now be described with reference to the accompanying drawings. The X-ray CT system, for example, includes a gantry shared by a plurality of modalities each including a couch, and switches movement control and UI display in accordance with the combination of modalities with the gantry. However, the embodiment is not limited to this, and the X-ray CT system need only be able to prevent an operation error for the operation unit of the gantry by control of the control circuitry. For example, the control circuitry may be configured to fix the UI display on the operation unit and control the moving direction of the gantry, or may be configured to switch the UI display on the operation unit and control the moving direction according to the UI display. In addition, since it is only necessary to finally control the moving direction, the timing to switch the moving direction can be a timing during or after carrying of the gantry, or immediately after the generation of the command signal. In this X-ray CT system, an X-ray CT apparatus and an arbitrary modality can be combined. Modalities that can be combined include, for example, a modality with a self-propelled gantry system such as an angio-CT apparatus or an operating table and a system including a couch moving base mechanism such as an X-ray CT apparatus and a PET (Positron Emission Tomography)-CT apparatus. The number of couches sharing the gantry is an arbitrary plural number such as 2, 3, 4, . . . . An example in which the X-ray CT system is applied to a 2-room solution will be described first as the first embodiment. Note that if the X-ray CT system is applied to a multi-room solution with three or more rooms, the number of couches, rooms as the destination of carrying by the carrier unit, and the functions of the control circuitry may be expanded in accordance with the number of rooms, relative to the arrangement applied to the 2-room solution. An example in which the X-ray CT system is applied to a 4-room solution will be described next as the second embodiment. The following embodiments will be explained using an example in which one couch and one examination room are arranged in a one-to-one correspondence in a multi-room solution. However, the embodiment is not limited to this, and is applicable to a case in which a plurality of couches and one examination room correspond to each other. An "examination room" may simply be called a "room".

First Embodiment

FIG. 1 is a block diagram showing the arrangement of an X-ray CT system according to the first embodiment. In an X-ray CT system 1 according to this embodiment, a plurality of modalities provided in a plurality of examination rooms share a gantry 2 used to execute X-ray CT (computed tomography) imaging for a subject. In other words, in the X-ray CT system 1, the gantry 2 is shared by a plurality of examination rooms R1 and R2, and the gantry 2 is shared by a plurality of couches 4 and 7. The examination room R1 and the couch 4 may be called a first room and a first couch, respectively. The examination room R2 and the couch 7 may be called a second room and a second couch, respectively. The gantry 2 is provided to be movable between the plurality of examination rooms R1 and R2 using a carrier apparatus and carrying rails L1_2. Note that the suffix of different numbers "1_2" of the carrying rail L1_2 represents the different examination rooms R1 and R2 corresponding to the different numbers. This also applies to suffixes for other rails and suffixes for sensors. Consoles 3 and 6 are individually provided for the couches 4 and 7. An opening/closing door 9 is provided on the moving path of the gantry 2 between the plurality of examination rooms, thereby keeping the independence of each examination room while ensuring the moving path for the gantry 2 at the time of a movement. Opening/closing of the opening/closing door 9 may be controlled from the consoles 3 and 6 or from the gantry 2 in accordance with the carrying of the gantry 2. Alternatively, the opening/closing door 9 may be an automatic door configured to automatically open/close in accordance with the carrying of the gantry 2. In addition, a sensor s1_2 is provided between the examination rooms so that the examination room in which the gantry 2 exists can be discriminated from sensor information. More specifically, for example, the sensor s1_2 is provided on the floor at a position where the moving path of the gantry intersects the opening/closing door 9, thereby detecting the gantry 2 that is being carried. The sensor s1_2 detects that the gantry 2 is being carried to the examination room R1 or R2 and may therefore be called a gantry detector. The sensor s1_2 need only detect the gantry 2 and, for example, a photosensor or the like is usable. The sensor s1_2 need not always be placed on the floor. Other sensors to be described later also need only detect the gantry 2. When placing the sensor s1_2 on the floor, it is placed at the time of, for example, installation of the X-ray CT apparatus and the X-ray angio-CT apparatus. The sensor s1_2 need only be arranged between the couches 4 and 7 spaced apart from each other and detect the gantry 2 that is being carried. That is, the sensor s1_2 need not always be arranged at the boundary between the examination rooms.

FIG. 1 shows a 2-room CT configuration in which the gantry 2 is shared by two modalities. For example, an X-ray CT apparatus capable of capturing a still image of a tomographic plane or the like is provided in one examination room R1. The X-ray CT apparatus includes the gantry 2 shared with an X-ray angio-CT apparatus, the CT console 3, and the couch 4. The couch 4 includes a couch top T1. The X-ray CT apparatus and the X-ray angio-CT apparatus can communicate with each other by, for example, CAN (Controller Area Network) communication. This also applies to the following embodiments. The arrangement of the X-ray CT apparatus will be described later with reference to FIG. 3.

An X-ray angio-CT apparatus that combines the X-ray CT apparatus with an angio apparatus capable of capturing a two-dimensional moving image of a blood vessel or the like is provided in the other examination room R2. The X-ray angio-CT apparatus includes the gantry 2 shared with the X-ray CT apparatus, an X-ray imaging apparatus 5, an X-ray console 6, and the couch 7. The couch 7 includes a couch top T2. The arrangement of the X-ray angio-CT apparatus will be described later with reference to FIG. 3.

Figure 2:
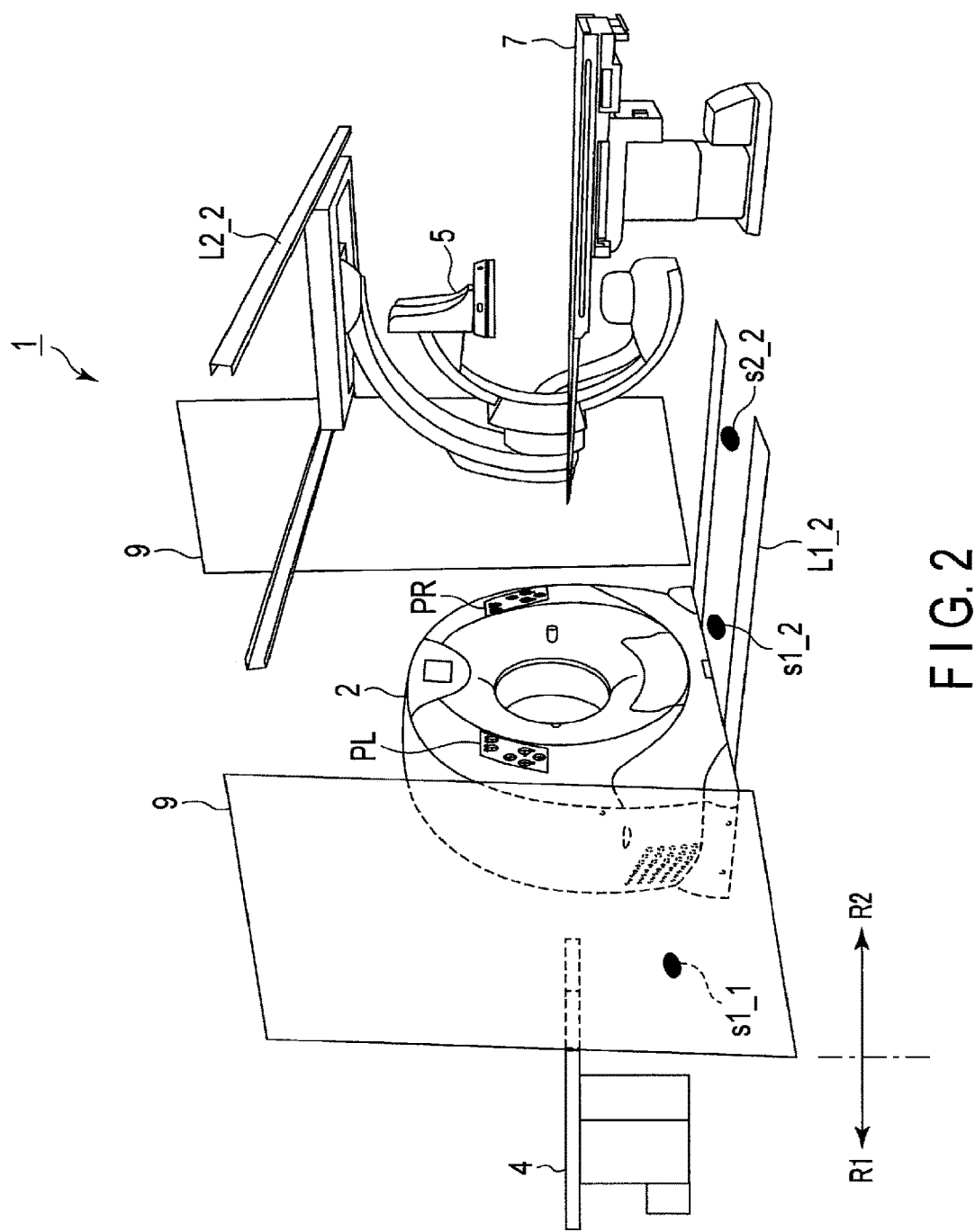
FIG. 2 is a perspective view showing the outer appearance of an X-ray CT system 1 viewed from the side of an examination room R2 shown in FIG. 1.

FIG. 2 is a perspective view showing the outer appearance of the X-ray CT system 1 viewed from the side of the examination room R2 shown in FIG. 1. The components of the X-ray CT system 1 according to this embodiment are arranged as shown in FIG. 2. In the examination room R2, a sensor s2_2 configured to detect the initial position of the gantry 2 is arranged, for example, on the floor at a position where the carrying rails L1_2 are close to the couch 7. Note that the suffix of the same number "2_2" of the sensor s2_2 represents only the examination room "R2" corresponding to the same number. This also applies to suffixes for other sensors and suffixes for rails. Additionally, in the examination room R1, a sensor s1_1 configured to detect the initial position of the gantry 2 is arranged on the floor at a position where the carrying rails L1_2 are close to the couch 4. The X-ray imaging apparatus 5 is arranged to be able to approach or retract with respect to the couch 7 via rails L2_2 provided on the ceiling along a direction orthogonal to the moving path of the gantry 2. The gantry 2 includes operation panels (not shown) on the left and right sides of the front surface facing the side of the couch 4, and includes operation panels PL and PR on the left and right sides of the back surface facing the side of the couch 7. The arrangements of the operation panels PL and PR are identical to each other. The operation panels are provided at a plurality of points so that they can be operated from any of the left and right sides of the front surface of the gantry 2 and the left and right sides of the back surface of the gantry 2. The arrangement of the components shown in FIG. 2 can appropriately be changed in accordance with the types of modalities to be used or the placement environment. For example, the carrying rails L1_2 are arbitrary additional items and may be omitted. This is because the carrier unit (not shown) need only be able to carry the gantry 2 by the driving force of the motor, and the gantry 2 need not always travel on the carrying rails L1_2.

In addition, the rails L2_2 on the ceiling may be omitted by providing a floor traveling type X-ray imaging apparatus in place of the ceiling traveling type X-ray imaging apparatus 5. Furthermore, the examination room or couch with the gantry 2 may be detected using the sensor s1_1 or S2_2 arranged near the couch 4 or 7 in place of the sensor s1_2 between the examination rooms R1 and R2.

Figure 3:
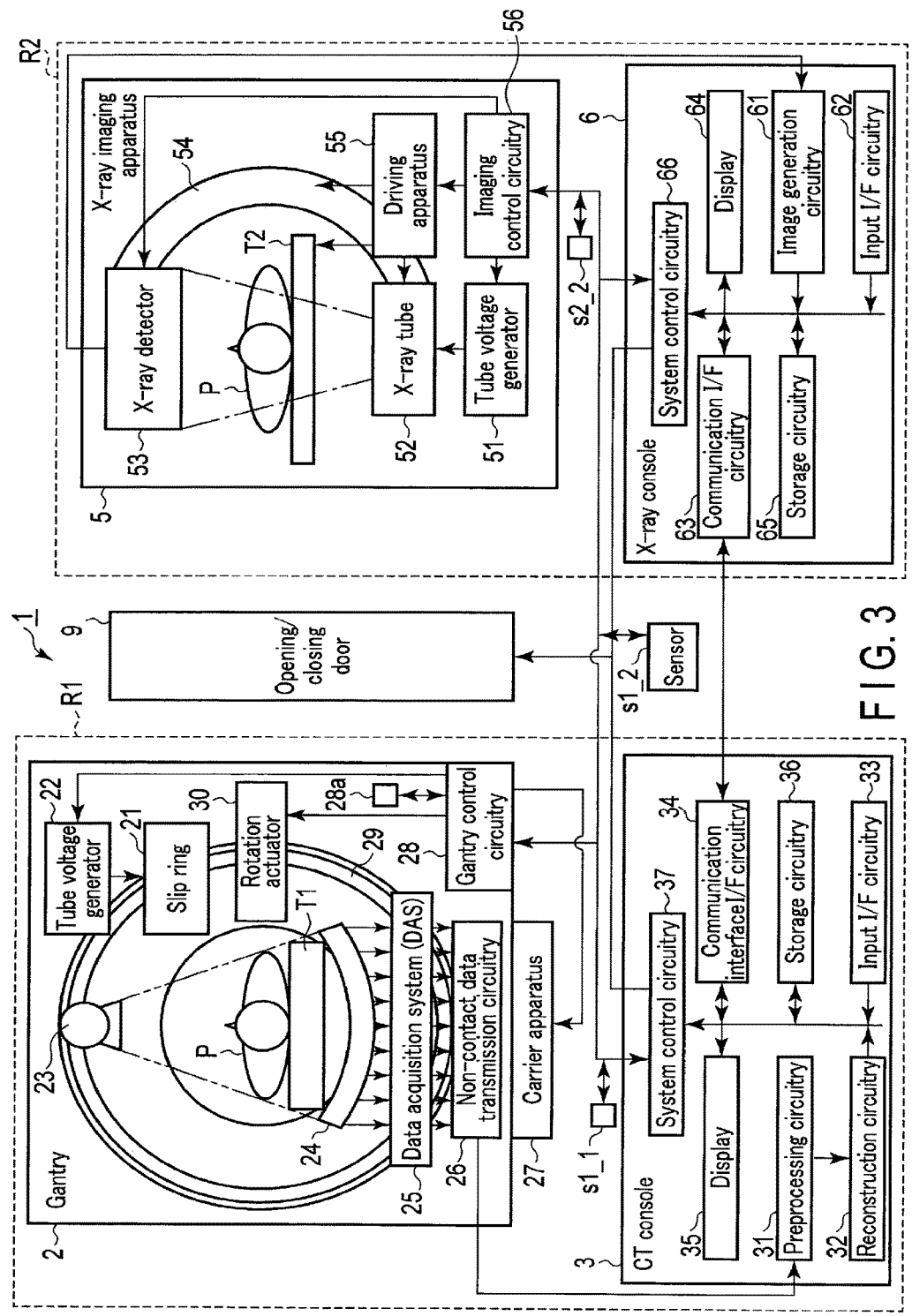
FIG. 3 is a block diagram showing the arrangement of an X-ray CT apparatus and an X-ray angio-CT apparatus provided in the X-ray CT system according to the embodiment.

FIG. 3 is a block diagram showing the arrangement of the X-ray CT apparatus and the X-ray angio-CT apparatus provided in the X-ray CT system 1 according to the embodiment. The X-ray CT apparatus, the X-ray angio-CT apparatus, the opening/closing door 9, and the sensors s1_1, s1_2, and s2_2 can communicate with each other via a network. The X-ray CT apparatus will be described first.

As shown in FIG. 3, the X-ray CT apparatus includes the gantry 2, the CT console 3, and the couch 4. The gantry 2 includes a slip ring 21, a tube voltage generator 22, an X-ray tube 23, an X-ray detector 24, a DAS (Data Acquisition System) 25, non-contact data transmission circuitry 26, a carrier apparatus 27, an operation unit 28a, and gantry control circuitry 28. The gantry 2 includes a rotary ring 29, a ring support mechanism that rotatably supports the rotary ring 29 about a subject's body axis (z-axis) serving as a rotation axis, and a rotation actuator (electric motor) 30 that rotates the rotary ring 29. The couch top T1 on which a subject P can lie is inserted into the opening portion of the rotary ring 29. The couch top T1 is supported by the couch 4 to be movable along the center axis of the rotary ring 29. The couch top T1 is aligned such that the body axis of the subject P lying on the couch top T1 matches the center axis of the rotary ring 29. The tube voltage generator 22, the X-ray tube 23, the X-ray detector 24, the DAS 25, the non-contact data transmission circuitry 26, a cooling apparatus (not shown), and the like are mounted on the rotary ring 29. Under the control of the CT console 3 via the gantry control circuitry 28, the tube voltage generator 22 generates a tube voltage to be applied to the X-ray tube 23, and a filament current to be supplied to the X-ray tube 23.

The X-ray tube 23 receives application of the tube voltage and supply of the filament current from the tube voltage generator 22 via the slip ring 21. The X-ray tube 23 emits X-rays from the focal point of the X-rays to the subject P lying on the couch top T1. The X-ray tube 23 generates X-rays having an energy spectrum corresponding to the tube voltage applied by the tube voltage generator 22. The X-rays emission range is indicated by the two-dot dashed line in FIG. 3.

The X-ray detector 24 is attached to the rotary ring 29 at a position and angle at which the X-ray detector 24 faces the X-ray tube 23 across the rotation axis. The X-ray detector 24 includes a plurality of light-receiving bands configured to detect X-rays emitted by the X-ray tube 23. An explanation will be made here assuming that a single light-receiving band forms a single channel. The plurality of channels are orthogonal to the rotation axis and are two-dimensionally arrayed in two directions, that is, a Z direction (slice direction) and an arc direction (channel direction) having, as a radius, a distance from the center located at the focal point of the emitted X-rays to the center of a light-receiving band corresponding to one channel. The DAS 25 is connected to the output side of the X-ray detector 24. In the X-ray detector 24, a plurality of light-receiving bands are arrayed in a line. At this time, the plurality of light-receiving bands are one-dimensionally arrayed almost in the arc direction along the channel direction. The plurality of light-receiving bands may be two-dimensionally arrayed in two directions, that is, the channel direction and the slice direction. That is, the two-dimensional array may be formed by arranging the plurality of channels one-dimensionally arrayed along the channel direction in a plurality of lines in the slice direction.

The DAS 25 attaches, for each channel, an IV converter configured to convert the current signal of each channel of the X-ray detector 24 into a voltage signal, an integrator configured to periodically integrate the voltage signals in synchronism with the X-ray radiation period, an amplifier configured to amplify the output of the integrator, and an analog to digital converter configured to convert the output signal of the amplifier into a digital signal. The DAS 25 transmits output data (pure raw data) to the CT console 3 via the non-contact data transmission circuitry 26 using magnetic transmission/reception or optical transmission/reception.

The carrier apparatus 27 is an apparatus that includes a motor and can carry the gantry 2 to each of the plurality of couches 4 and 7. The carrier apparatus 27 can carry the gantry 2 between the plurality of examination rooms R1 and R2 using, for example, the carrying rails L1_2 provided in the examination rooms. When carrying the gantry 2 to the examination room R1, the carrier apparatus 27 arranges the gantry 2 in an orientation in which the front side of the gantry 2 faces the couch 4. When carrying the gantry 2 to the examination room R2, the carrier apparatus 27 arranges the gantry 2 in an orientation in which the back side of the gantry 2 faces the couch 7. The carrier apparatus 27 may carry the gantry 2 in an almost constant orientation. That is, the orientation of the gantry 2 arranged in the examination room R1 and the orientation of the gantry 2 arranged in the examination room R2 only need be almost the same, and the orientation of the gantry 2 during carrying need not be almost constant.

The operation unit 28a generates various kinds of movement commands in accordance with an operation on the operation panels PL and PR by the operator, and inputs a generated movement command to the gantry control circuitry 28. The various kinds of movement commands include, for example, a tilt movement command (a command signal to command a tilt movement) and a movement command for a movement in a certain direction (a command signal to command a relative movement of the gantry 2 and the couch 4 (or 7)). The operation unit 28a has a positive/negative display of the direction of a tilt movement and a positive/negative display of the moving amount of a tilt movement. On the operation unit 28a, at least one display of the positive/negative displays concerning a tilt movement is switched by the gantry control circuitry 28. Similarly, the operation unit 28a has a positive/negative display of the direction of a relative movement of the gantry 2 and the couch 4 (or 7) and a positive/negative display of the moving amount of a relative movement. On the operation unit 28a, at least one of the positive/negative displays concerning a relative movement is switched by the gantry control circuitry 28. Note that the positive/negative display of the direction may be called, for example, a forward/reverse display of the direction. The arrangements of the operation panels PL and PR of the operation unit 28a are identical to each other. Hence, an explanation will be made here using the operation panel PL on the left side as an example.

Figure 4:
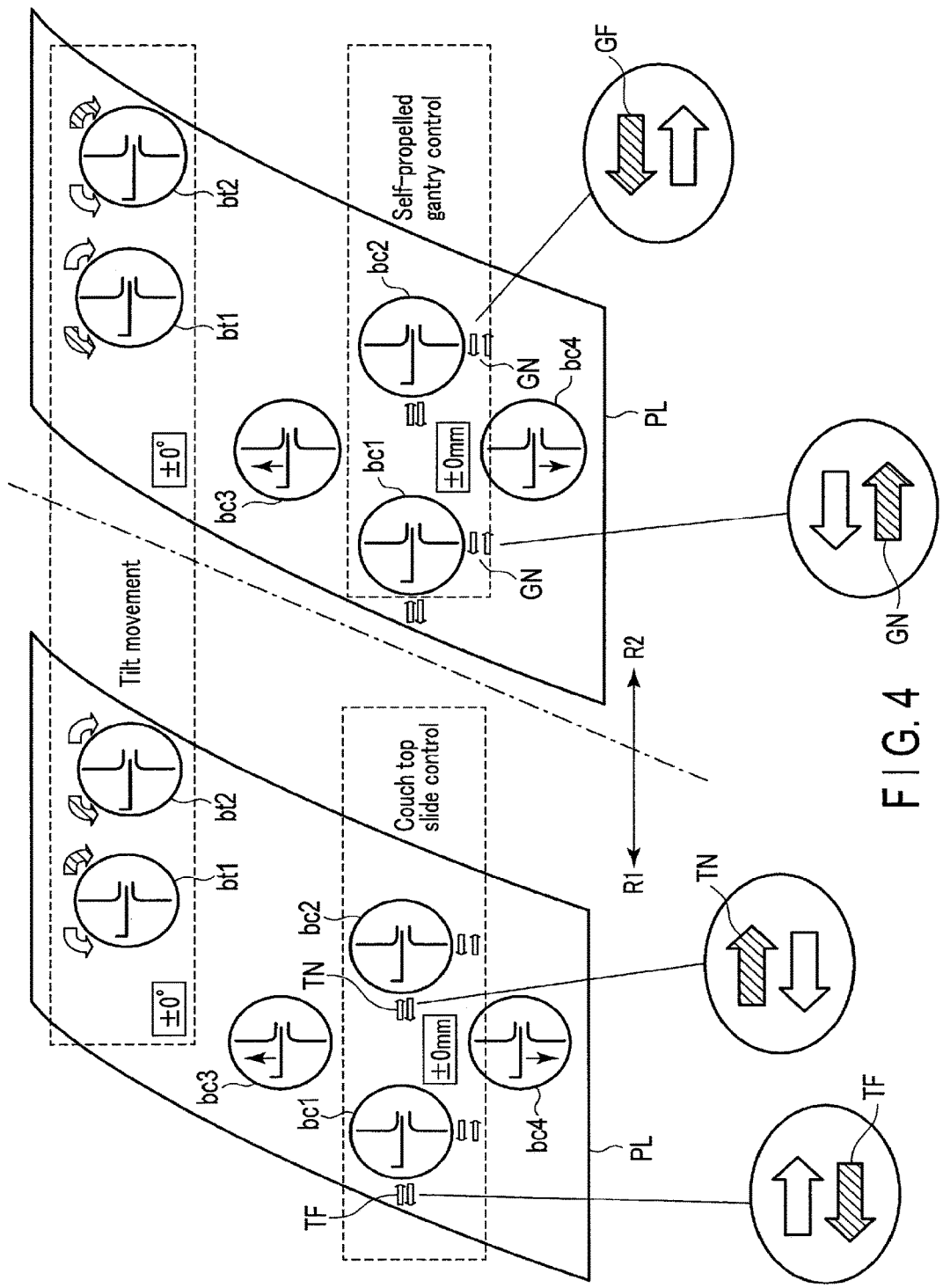
FIG. 4 is a schematic view for explaining an operation panel PL according to the embodiment.
Figure 5:
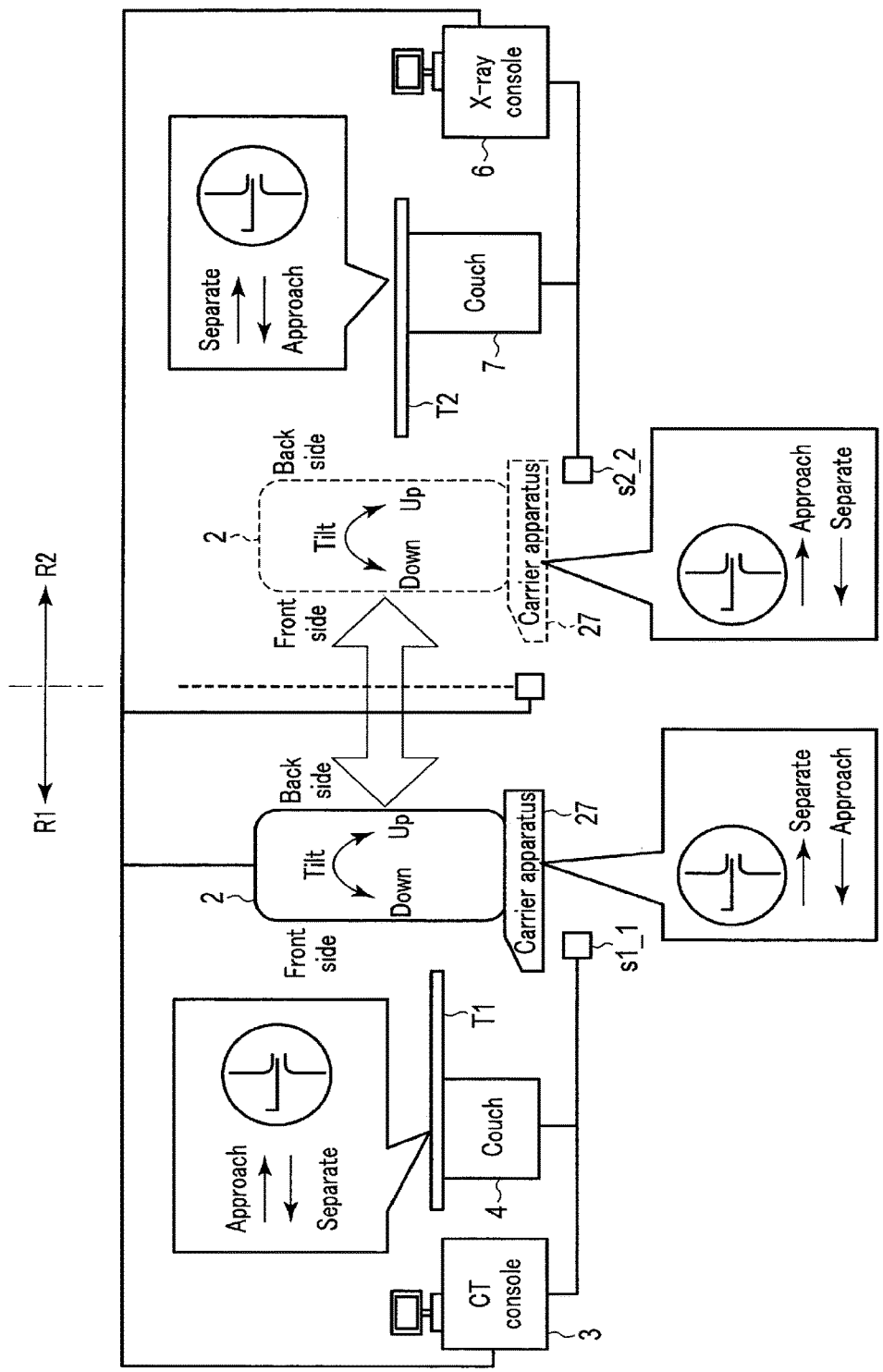
FIG. 5 is a schematic view showing that the approaching direction, the separating direction, and the tilt direction are reversed between examination rooms R1 and R2 according to the embodiment.

FIG. 4 is a schematic view for explaining the operation panel PL in the examination rooms R1 and R2. FIG. 5 is a schematic view showing that the approaching direction/separating direction between the gantry and the couch and the tilt direction of the gantry are reversed between the examination rooms R1 and R2. For example, the approaching direction (rightward on the sheet surface) of the couch 4 in the examination room R1 corresponds to the separating direction (rightward on the sheet surface) of the couch 7 in the examination room R2. In addition, the separating direction (leftward on the sheet surface) of the couch 4 in the examination room R1 corresponds to the approaching direction (leftward on the sheet surface) of the couch 7 in the examination room R2.

Similarly, the approaching direction (leftward on the sheet surface) of the gantry 2 in the examination room R1 corresponds to the separating direction (leftward on the sheet surface) of the gantry 2 in the examination room R2. In addition, the separating direction (rightward on the sheet surface) of the gantry 2 in the examination room R1 corresponds to the approaching direction (rightward on the sheet surface) of the gantry 2 in the examination room R2.

Similarly, the upward tilting direction (clockwise on the sheet surface) of the gantry 2 in the examination room R1 corresponds to the downward tilting direction (clockwise on the sheet surface) of the gantry 2 in the examination room R2. In addition, the downward tilting direction (counterclockwise on the sheet surface) of the gantry 2 in the examination room R1 corresponds to the upward tilting direction (counterclockwise on the sheet surface) of the gantry 2 in the examination room R2.

Display control of the operation panel PL is done by the gantry control circuitry 28 so no mismatch occurs in the UI display due to the above-described difference in direction between the examination rooms R1 and R2. More specifically, each button on the operation panel PL has the pictograms of the gantry and the couch top and are implemented as hardware capable of coping with various patterns. One or two sets of lamps in arrow shapes in directions opposite to each other are arranged near each button. When one lamp of the one or two sets of lamps is displayed (turned on), the pictogram of the couch top or gantry located near the displayed arrow represents the moving target, and the direction of the displayed arrow represents the moving direction.

On the operation panel PL, at least one of the interpretation of a button and the direction of a displayed arrow is switched from the viewpoint of preventing any mismatch. For example, if the moving direction does not match for the same moving target, the interpretation of a button is switched from the viewpoint of preventing a mismatch between the button operation and the moving direction. Then, even if a button that causes a mismatch is pressed, no mismatch occurs because the interpretation of the button is changed. Alternatively, if the direction of the displayed arrow is switched, a button that does not cause a mismatch is pressed according to the guidance of the arrow, and no mismatch occurs. If the moving direction does not match for a different moving target, the display position of the arrow is switched to the vicinity of the pictogram of the moving target. In addition, the interpretation of a button or the direction of an arrow is switched in accordance with the moving direction, as described above.

The operation panel PL includes a first tilt movement button bt1 and a second tilt movement button bt2, each of which has arrows representing tilting directions displayed in the vicinity, and a positive/negative display (±0° in FIG. 4) of a tilt moving amount. The display of the arrows means, for example, one of two lamps that are arranged for each button and have arrow shapes in directions opposite to each other is turned on. The positive/negative display portion of the tilt moving amount displays, for example, a moving amount to tilt the opening portion of the gantry 2 upward with respect to the couch as positive and a moving amount to tilt the opening portion downward as negative. The operation panel PL also includes a first movement button bc1 and a second movement button bc2, a couch top separation lamp TF in an arrow shape facing left on the sheet surface, a couch top approach lamp TN in an arrow shape facing right on the sheet surface, a gantry approach lamp GN in an arrow shape facing right on the sheet surface, a gantry separation lamp GF in an arrow shape facing left on the sheet surface, and a positive/negative display portion (±0 mm in FIG. 4) of the moving amount in the moving direction. The positive/negative display portion of the moving amount in the moving direction displays, for example, a moving amount in a direction in which the couch and the gantry approach as positive and a moving amount in a direction in which the couch and the gantry separate as negative. The operation panel PL also includes a couch top raising button bc3 and a couch top lowering button bc4.

In the examination rooms R1 and R2, the first tilt movement button bt1 and the second tilt movement button bt2 are common. However, the arrow in the reference direction displayed near each of the buttons bt1 and bt2 is erased (turned off), and the arrow in the opposite direction is displayed (turned on).

That is, in the examination room R1, the first tilt movement button bt1 inputs a tilt movement command to tilt the opening portion of the gantry 2 upward with respect to the couch to the gantry control circuitry 28 in accordance with the pressing operation of the operator. The second tilt movement button bt2 inputs a tilt movement command to tilt the opening portion of the gantry 2 downward with respect to the couch to the gantry control circuitry 28 in accordance with the pressing operation of the operator.

In the examination room R2, the first tilt movement button bt1 inputs a tilt movement command to tilt the opening portion of the gantry 2 downward with respect to the couch to the gantry control circuitry 28 in accordance with the pressing operation of the operator. The second tilt movement button bt2 inputs a tilt movement command to tilt the opening portion of the gantry 2 upward with respect to the couch to the gantry control circuitry 28 in accordance with the pressing operation of the operator.

In the examination room R1, couch top slide control in X-ray CT is executed. Hence, the couch top separation lamp TF is displayed (turned on) near the first movement button bc1, and the couch top approach lamp TN is displayed (turned on) near the second movement button bc2 under the control of the gantry control circuitry 28. At this time, the first movement button bc1 inputs a movement command to move the couch top in the separating direction with respect to the gantry 2 to the gantry control circuitry 28 in accordance with the pressing operation of the operator. The second movement button bc2 inputs a movement command to move the couch top in the approaching direction with respect to the gantry 2 to the gantry control circuitry 28 in accordance with the pressing operation of the operator.

In the examination room R2, self-propelled gantry control in X-ray angio-CT is executed. Hence, the gantry approach lamp GN is displayed (turned on) near the first movement button bc1, and the gantry separation lamp GF is displayed (turned on) near the second movement button bc2 under the control of the gantry control circuitry 28. At this time, the first movement button bc1 inputs a movement command to move the gantry 2 in the approaching direction with respect to the couch to the gantry control circuitry 28 in accordance with the pressing operation of the operator. The second movement button bc2 inputs a movement command to move the gantry 2 in the separating direction with respect to the couch to the gantry control circuitry 28 in accordance with the pressing operation of the operator.

In the examination rooms R1 and R2, the couch top raising button bc3 and the couch top lowering button bc4 are common.

The gantry control circuitry 28 controls the tube voltage generator 22, the carrier apparatus 27, the operation unit 28a, the rotation actuator 30, and the like in accordance with a control signal output from the CT console 3, output signals of the sensors s1_2, s1_1, and s2_2, and a movement command input from the operation unit 28a. The gantry control circuitry 28 includes a processing device (processor) such as a CPU or MPU, and storage devices (memories) such as a ROM and a RAM as hardware resources. The gantry control circuitry 28 may be implemented by an ASIC, FPGA, CPLD, or SPLD. The processing device reads out a program saved in the storage device and executes it, thereby implementing the above-described functions. Note that instead of saving the program in the storage device, the program may be incorporated directly in circuitry of the processing device. In this case, the processing device reads out the program incorporated in the circuitry and executes it, thereby implementing the above-described functions.

Here, the sensor s1_2 is arranged between the couches 4 and 7 and detects the gantry 2 that is being carried. In this example, the sensor s1_2 is arranged at the boundary between the examination rooms R1 and R2. Upon detecting the gantry 2 that is being carried from the examination room R1 to the examination room R2, the sensor s1_2 transmits an output signal "1" to the gantry control circuitry 28 in place of an output signal "0", as shown in FIG. 6. The gantry control circuitry 28 holds the value "1" of the output signal in the memory as sensor information. The held sensor information is used to read out control information to be described later.

The memory may store a table in which an assumed system combination is associated with sensor information in advance. For example, the carrying destination of the gantry 2, the orientation of the gantry 2 after carrying, the moving direction of the gantry 2 or couch top, and the tilting direction of the gantry 2 may be stored in association. For example, the memory may store sensor information representing the value of the output signal of the sensor s1_2, the orientation of the gantry 2 with respect to a couch, a couch, an examination room, and control information in association, as shown in FIG. 7. At this time, the orientation of the gantry 2, the couch, the examination room, and the control information associated with the sensor information in advance can be read out based on the held sensor information. For the examination room R1 corresponding to sensor information "0", the control information represents couch top slide control in the reference direction and tilt movement control in the reference direction. For the examination room R2 corresponding to sensor information "1", the control information represents self-propelled gantry control in the opposite direction and tilt movement control in the opposite direction. Note that in this example, the reference direction and opposite direction are associated with the examination rooms R1 and R2, respectively. However, the embodiment is not limited to this, and the opposite direction and the reference direction may be associated with the examination rooms R1 and R2, respectively. Additionally, couch top slide control is associated with the CT couch. However, the embodiment is not limited to this, and self-propelled gantry control may be associated with CT couch. Similarly, self-propelled gantry control is associated with the angio couch. However, the embodiment is not limited to this, and couch top slide control may be associated with angio couch. The memory need not always store all pieces of information shown in FIG. 7 in association. For example, to control the direction of a tilt movement, the memory stores a room to arrange the gantry 2 and the direction of the tilt movement in association. Alternatively, to control a relative movement, the memory stores a room to arrange the gantry 2 and the direction of the relative movement in association. That is, the memory stores the carrying destination of the gantry 2 and control information in association. As the carrying destination, either an examination room or a couch can be used. The memory stores sensor information and control information in association.

When a gantry control program is installed from outside, the memory stores the gantry control program. The gantry control program is, for example, a program configured to cause the gantry control circuitry 28 serving as a computer provided in by the gantry 2 to implement following control functions (f1) and (f2). Note that the control functions (f1) and (f2) may be implemented like a switching function (sc).

(f1) A first control function of controlling the direction of the tilt movement of the gantry 2 in accordance with the room where the gantry 2 is arranged during generation of a tilt movement command (a command signal to command a tilt movement) by the operation unit 28a. Note that the first control function f1 may control the direction of the tilt movement based on, for example, contents stored in the memory. Additionally, using, for example, a detection result of the sensor s1_2 as a trigger, the first control function f1 may switch the direction of the tilt movement corresponding to the room to which the gantry 2 is carried, and control the direction of the tilt movement of the gantry based on the switched direction during generation of the command signal.

(f2) A second control function of controlling the direction of the relative movement of the gantry 2 and the couch 4 (or 7) in accordance with the room where the gantry 2 is arranged during generation of a movement command for a certain direction (a command signal to command a relative movement) by the operation unit 28a. Concerning the relative movement of the gantry 2 and the couch 4 (or 7), the couch 4 may be replaced with the couch top T1, and the couch 7 may be replaced with the couch top T2. The second control function f2 may control the direction of the relative movement based on, for example, contents stored in the memory. Additionally, using, for example, a detection result of the sensor s1_2 as a trigger, the second control function f2 may switch the direction of the relative movement corresponding to the room to which the gantry 2 is carried, and control the direction of the relative movement based on the switched direction during generation of the command signal.

(sc) A switching function of switching, during carrying of the gantry 2, at least one of the moving direction of the gantry 2 or the couch top T1 after the carrying and the display of the moving direction in accordance with the carrying destination of the gantry 2 and the orientation of the gantry 2 after the carrying. If the gantry control circuitry 28 has the switching function sc, the switching function may be implemented as a function of, for example, switching the moving direction to the front side or back side in accordance with the carrying destination of the gantry 2 and the orientation of the gantry 2 after the carrying even if the same control signal (for example, a movement command to the front side in FIG. 5) is received from the console. That is, the switching function sc may be implemented as an interpretation function of interpreting a received control signal, and if the control signal causes a mismatch, converting it into a control signal that causes no mismatch and outputting it to the carrier apparatus 27. The switching function sc may be implemented as a display switching function of switching the display of the moving direction such that a control signal that causes no mismatch is input. The switching function sc may be implemented as a function of switching the display position of the moving direction in accordance with a moving target in addition to the interpretation function or the display switching function. The switching function sc may execute the switching control based on the above-described contents (the carrying destination and the orientation and moving direction of the gantry) stored in the memory. The switching function sc may switch the tilting direction of the gantry 2 after carrying in accordance with the orientation of the gantry after the carrying. The switching function sc may execute the switching control of the tilting direction of the gantry 2 based on the above-described contents (the carrying destination, the orientation of the gantry, the moving direction, and the tilting direction) stored in the memory. The switching function sc may execute the switching control using a detection result (for example, a change from the output signal "0" to the output signal "1") of the sensor s1_2 as a trigger.

When performing switching control of the above-described display contents on the operation panels PL and PR, the switching function sc may switch the display of one of the positive/negative display of the moving amount in the moving direction, the display of the tilting direction, and the positive/negative display of the moving amount in the tilting direction. Additionally, the switching function sc may switch the display of the moving direction, as described above. As described above, the switching function sc may switch at least one of the positive/negative display of the direction of the tilt movement and the positive/negative display of the moving amount of the tilt movement provided on the operation unit 28a in accordance with the room where the gantry 2 is arranged. Similarly, the switching function sc may switch at least one of the positive/negative display of the direction of the relative movement and the positive/negative display of the moving amount of the relative movement provided on the operation unit 28a in accordance with the room where the gantry 2 is arranged.

Figure 8:
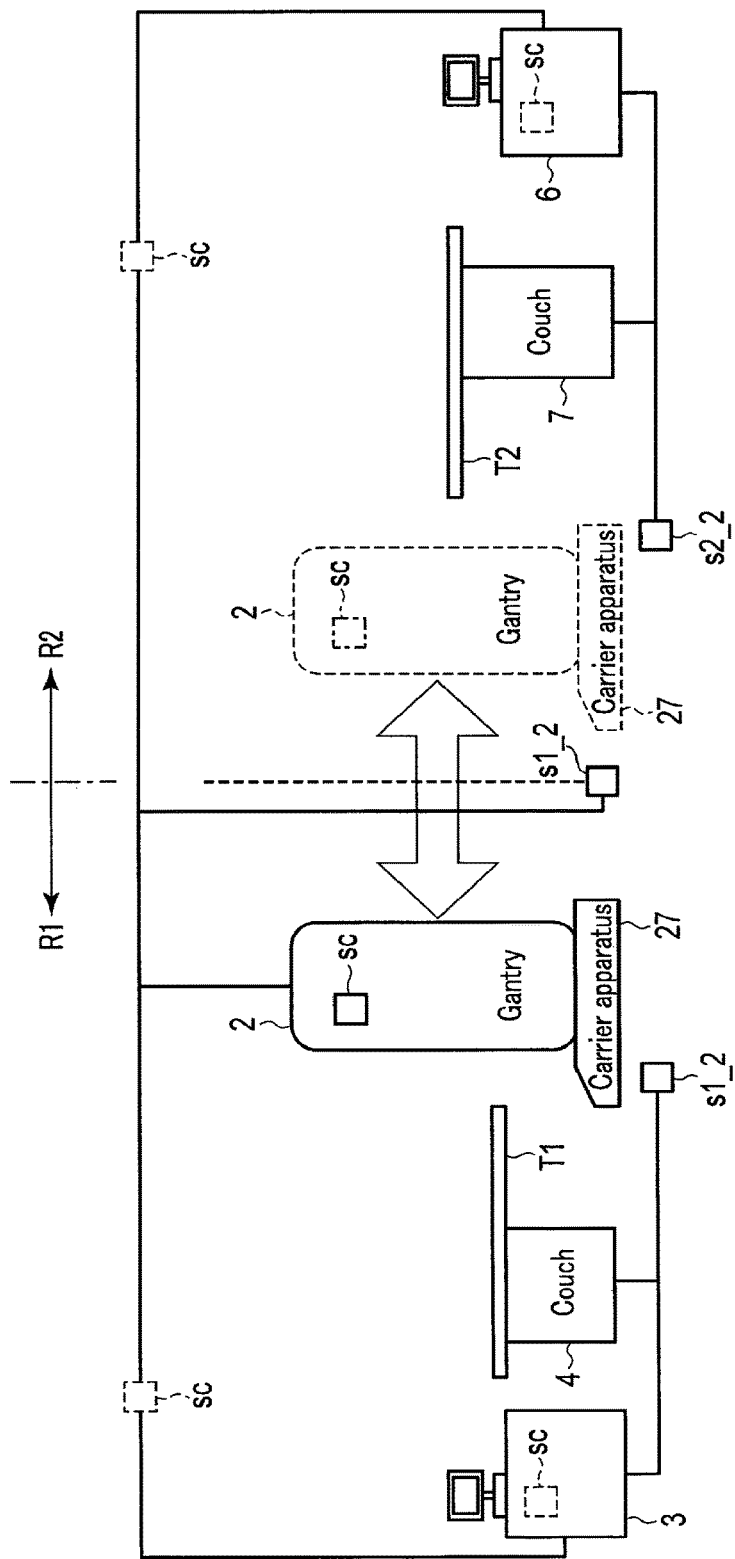
FIG. 8 is a schematic view showing an example of implementation of a switching function sc according to the embodiment.

Note that as shown in FIG. 8, the switching function sc need not always be arranged in the above-described gantry 2, and can be arranged in an arbitrary location on the path of a control signal transmitted from the console 3 or 6 to the gantry 2, for example, in the system control circuitry 37 of the CT console 3, in system control circuitry 66 of the X-ray console 6, or a device arranged between the gantry 2 and the console 3 or 6. If the switching function sc is implemented in a device arranged between the gantry 2 and the console, the switching function sc may be implemented not in a plurality of devices but in one device that generally controls the multi-room solution. In addition, the switching function sc may be implemented as a program configured to cause a computer to implement the function, or may be implemented in the gantry or console as hardware control circuitry configured to execute the function. The above description of the arrangement and implementation of the switching function sc also applies to the control functions f1 and f2 and the following embodiments.

The CT console 3 includes preprocessing circuitry 31, reconstruction circuitry 32, input interface (I/F) circuitry 33, communication interface (I/F) circuitry 34, a display 35, storage circuitry 36, and system control circuitry 37.

The preprocessing circuitry 31 performs preprocessing for pure raw data output from the non-contact data transmission circuitry 26. Preprocessing includes, for example, logarithmic transformation processing for the pure raw data, sensitivity unevenness correction processing between channels, and processing of correcting an extreme decrease in signal strength or signal loss caused by a strong X-ray absorber, mainly, a metal portion. The preprocessing circuitry 31 transmits the data (called raw data or projection data and representing projection data here) immediately before reconstruction processing, which has undergone the preprocessing, to the reconstruction circuitry 32 and the storage circuitry 36 in association with data representing a view angle at the time of data acquisition. Note that the data immediately before reconstruction processing, which has undergone the preprocessing, is called raw data or projection data. In this embodiment, the data immediately before reconstruction processing will be referred to as projection data.

Projection data is a set of data values according to the intensity of X-rays transmitted through the subject. For the descriptive convenience, a set of projection data of all channels, which are acquired almost simultaneously by one shot and have the same view angle, will be referred to as a projection data set. The view angle represents each position of the circular orbit of the X-ray tube 23 rotating about the rotation axis serving as the center as an angle within the range of 360° with respect to the uppermost portion (0°) of the circular orbit vertically raising from the rotation axis. Note that projection data in the projection data set corresponding to each channel is identified by a view angle, a cone angle, and a channel number.

Based on, for example, the projection data set within the view angle range of 360° or 180°+fan angle, which is transmitted from the preprocessing circuitry 31, the reconstruction circuitry 32 reconstructs almost columnar volume data by the Feldkamp method or cone-beam reconstruction method. The reconstruction circuitry 32 is formed from, for example, memories and a predetermined processor. The reconstruction circuitry 32 also reconstructs a two-dimensional CT image (a tomographic image to be simply referred to as a CT image hereinafter) from the projection data set by, for example, fan-beam reconstruction (also called fan-beam convolution back projection) FBP (Filtered Back Projection), or iterative reconstruction. The Feldkamp method is a reconstruction method used when projection rays intersect a reconstructed plane like a cone-beam. This is an iterative image reconstruction method in which assuming that the cone angle is small, processing is performed by regarding the beam as a fan projection beam at the time of convolution, and back projection is processed along rays in scanning. The cone-beam reconstruction is a method capable of suppressing a cone angle error as compared to the Feldkamp method. This is a reconstruction method of correcting projection data in accordance with the angle of a ray with respect to a reconstructed plane. The reconstruction circuitry 32 transmits the reconstructed volume data to the storage circuitry 36. The reconstruction circuitry 32 transmits the reconstructed CT image to the storage circuitry 36.

The input interface circuitry 33 is implemented by a track ball, a switch button, a mouse, a keyboard, a touch pad configured to perform an input operation by a touch on an operation surface, or a touch panel display that integrates a display screen and a touch pad. The input interface circuitry 33 is connected to the system control circuitry 37. The input interface circuitry 33 converts an input operation received from the operator into an electrical signal and outputs it to the system control circuitry 37. Note that in this embodiment, the input interface circuitry 33 is not limited to circuitry including a physical operation component such as a track ball, a switch button, a mouse, or a keyboard. For example, electrical signal processing circuitry configured to receive an electrical signal corresponding to an input operation from an external input device provided separately from the apparatus and output the electrical signal to the system control circuitry 37 is also included in an example of the input interface circuitry 33.

The communication interface circuitry 34 is circuitry configured to communicate with an external device using one or both of wireless communication and wired communication. The external device is, for example, a modality, a server included in a system such as an RIS (Radiological Information System), an HIS (Hospital Information System), or a PACS (Picture Archiving and Communication System) or another workstation.

The display 35 displays various kinds of data, the above-described CT image, the above-described three-dimensional image, or the like on a display device under the control of the system control circuitry 37. As the display device, for example, a CRT display (Cathode Ray Tube Display), an LCD (Liquid Crystal Display), an OELD (Organic Electro Luminescence Display), a plasma display, or another arbitrary display known in this technical field can be used as needed.

The storage circuitry 36 includes an HDD (Hard Disk Drive) capable of storing a relatively large capacity data and an SSD (Solid State Drive). The storage circuitry 36 stores the CT image reconstructed by the reconstruction circuitry 32. The storage circuitry 36 stores the projection data transmitted from the preprocessing circuitry 31 and the volume data reconstructed by the reconstruction circuitry 32. The storage circuitry stores a control program configured to control the timing to apply a tube voltage to the X-ray tube 23.

Note that as the storage circuitry 36, not only a magnetic disk such as an HDD but also a magneto-optical disk or an optical disk such as a CD (Compact Disc) or a DVD (Digital Versatile Disc) can be used. The storage area of the storage circuitry 36 can exist in the X-ray CT system 1 or in an external storage device connected via a network.

The system control circuitry 37 includes the above-described processing devices and storage device as hardware resources. The system control circuitry 37 functions as the core of the X-ray CT apparatus. More specifically, the system control circuitry 37 reads out the control program stored in the storage circuitry 36, loads it onto the memory, and controls the units of the X-ray CT apparatus in accordance with the loaded control program.

The X-ray angio-CT apparatus will be described next. As shown in FIG. 3, the X-ray angio-CT apparatus includes the gantry 2 shared with the X-ray CT apparatus, the X-ray imaging apparatus 5, the X-ray console 6, and the couch 7.

The X-ray imaging apparatus 5 includes a tube voltage generator 51, an X-ray tube 52, an X-ray detector 53, a support mechanism 54, a driving apparatus 55, and imaging control circuitry 56.

The tube voltage generator 51 generates a tube current to be supplied to the X-ray tube 52 and a tube voltage to be applied to the X-ray tube 52. The tube voltage generator 51 supplies the tube current to the X-ray tube 52 and applies the tube voltage to the X-ray tube 52 in accordance with an X-ray imaging condition under the control of the X-ray console 6 via the imaging control circuitry 56.

The X-ray tube 52 generates X-rays from an X-ray focal point based on the tube current supplied from the tube voltage generator 51 and the tube voltage applied by the tube voltage generator 51. The X-rays generated from the X-ray focal point are emitted to the subject P via X-ray emission windows provided in the front surface of the X-ray tube 52.

The X-ray detector 53 detects the X-rays generated by the X-ray tube 52 and transmitted through the subject P. Electrical signals generated by a plurality of semiconductor elements in accordance with the incidence of the X-rays are output to an ADC (Analog to Digital Converter) (not shown). The ADC converts the electrical signals into digital data. The ADC outputs the digital data to image generation circuitry 61. Note that an image intensifier may be used as the X-ray detector 53.

The support mechanism 54 movably supports the X-ray tube 52 and the X-ray detector 53. More specifically, the support mechanism 54 includes, for example, a C-arm and a C-arm support portion (neither are shown). The X-ray tube 52 and the X-ray detector 53 are mounted on the C-arm to face each other. The C-arm support portion supports the C-arm slidably in a direction (to be referred to as a C direction hereinafter) along the C shape of the C-arm. The C-arm support portion is placed to be movable along the rails L2_2 provided on the ceiling. The rails L2_2 are provided on the ceiling along, for example, a direction orthogonal to the longitudinal direction of the couch top T2. The C-arm support portion supports the C-arm rotatably in a direction (to be referred to as a C orthogonal direction hereinafter) orthogonal to the C direction almost about a connecting portion that connects the C-arm and the C-arm support portion. Note that the C-arm support portion can also support the C-arm movably in parallel to the widthwise direction and the longitudinal direction of the couch top T2. In addition, the C-arm supports the X-ray tube 52 and the X-ray detector 53 such that the distance (SID: Source Image Distance) between the X-ray focal point and the X-ray detector 53 can be changed.

Note that the support mechanism 54 is not limited to the structure using the C-arm. The support mechanism 54 may have, for example, to arms (for example, robot arms) configured to support the X-ray tube 52 and the X-ray detector 53, respectively, movably in an arbitrary direction. The support mechanism 54 may have an Ω arm suspended from the ceiling in place of the C-arm. The support mechanism 54 may have a biplane structure. The support mechanism 54 is not limited to an over tube system and an under tube system, and can be applied to an arbitrary form.

The driving apparatus 55 drives the couch 7 and the support mechanism 54 under the control of the X-ray console 6. More specifically, the driving apparatus 55 supplies a drive signal according to a control signal from the system control circuitry 66 to the C-arm support portion to make the C-arm slide in the C direction and rotate in the C orthogonal direction. At the time of X-ray imaging, the subject P lying on the couch top T2 is arranged between the X-ray tube 52 and the X-ray detector 53.

The driving apparatus 55 drives the couch 7 under the control of the system control circuitry 66, thereby moving the couch top T2. More specifically, the driving apparatus 55 makes the couch top T2 slide in the widthwise direction or longitudinal direction of the couch top T2 based on the control signal of the system control circuitry 66. The driving apparatus 55 also vertically moves the couch top concerning the vertical direction. In addition, the driving apparatus 55 may rotate the couch top T2 to tilt the couch top T2 using at least one of the widthwise direction and the longitudinal direction as a rotation axis.

The imaging control circuitry 56 controls the tube voltage generator 51, the X-ray detector 53, the driving apparatus 55, and the like under the control of the system control circuitry 66 based on a command of the operator, the X-ray imaging direction, the X-ray emission range, the X-ray emission condition, and the like.

The X-ray console 6 includes the image generation circuitry 61, input interface circuitry 62, communication interface circuitry 63, a display 64, storage circuitry 65, and the system control circuitry 66.

The image generation circuitry 61 performs preprocessing for digital data output from the X-ray detector 53. Preprocessing includes, for example, sensitivity unevenness correction between channels in the X-ray detector 53, correction of an extreme decrease in signal strength or data loss caused by a strong X-ray absorber such as a metal. The image generation circuitry 61 generates an X-ray image based on the preprocessed digital data. The image generation circuitry 61 outputs the generated X-ray image to the display 64 and the storage circuitry 65.

The input interface circuitry 62 is implemented by a track ball, a switch button, a mouse, a keyboard, a touch pad configured to perform an input operation by a touch on an operation surface, or a touch panel display that integrates a display screen and a touch pad. The input interface circuitry 62 is connected to the system control circuitry 66. The input interface circuitry 62 converts an input operation received from the operator into an electrical signal and outputs it to the system control circuitry 66. Note that in this embodiment, the input interface circuitry 62 is not limited to circuitry including a physical operation component such as a track ball, a switch button, a mouse, or a keyboard. For example, electrical signal processing circuitry configured to receive an electrical signal corresponding to an input operation from an external input device provided separately from the apparatus and output the electrical signal to the system control circuitry 66 is also included in an example of the input interface circuitry 62.

The communication interface circuitry 63 is circuitry configured to communicate with an external device using one or both of wireless communication and wired communication. The external device is, for example, a modality, a server included in a system such as an RIS, an HIS, or a PACS or another workstation.

The display 64 displays various kinds of data, the above-described X-ray image, or the like on a display device under the control of the system control circuitry 66. As the display device, for example, a CRT display, an LCD, an OELD, a plasma display, or another arbitrary display known in this technical field can be used as needed.

The storage circuitry 65 stores the X-ray image generated by the image generation circuitry 61, the control program of the X-ray imaging apparatus 5, a diagnostic protocol, a command of the operator input from the input interface circuitry 62, various kinds of data groups such as imaging conditions and fluoroscopy conditions concerning X-ray imaging, an X-ray dose, and the like.

The system control circuitry 66 includes a CPU (Central Processing Unit) and memories (none are shown). The system control circuitry 66 temporarily stores pieces of information sent from the input interface circuitry 62 such as a command of the operator, the X-ray imaging position, the X-ray imaging direction by the X-ray tube 52, the X-ray emission range, and the X-ray emission condition in the memory (not shown). The system control circuitry 66 controls the tube voltage generator 51, the X-ray detector 53, the driving apparatus 55, and the like via the imaging control circuitry 56 to execute X-ray imaging in accordance with the command of the operator, the X-ray imaging direction, the X-ray emission range, the X-ray emission condition, and the like stored in the memory. In addition, the system control circuitry 66 controls the display 64 and the like.

The operation of the X-ray CT system having the above-described arrangement will be described next with reference to the flowchart of FIG. 9. The following explanation will be made mainly concerning the movement of the gantry 2 before CT examination. This also applies to the following embodiments.

First, assume that the gantry 2 is arranged in the examination room R1 serving as the reference in the examination rooms R1 and R1 of the 2-room solution. At this time, assume that the gantry 2 is moved from the couch 4 in the examination room R1 to the couch 7 in the examination room R2.

In the CT console 3 in the examination room R1, the system control circuitry 66 sends a gantry moving request to the gantry 2 (step ST1).

In the gantry 2, the gantry control circuitry 28 controls the carrier apparatus 27 based on the gantry moving request. The carrier apparatus 27 starts carrying the gantry 2 under the control of the gantry control circuitry 28. The gantry 2 thus moves (step ST2). During the carrying of the gantry by the carrier apparatus 27, the gantry control circuitry 28 inhibits the operation of the operator from the consoles 3 and 6 and the operation panels PL and PR (step ST3). However, the operation inhibited in step ST3 is an operation concerning CT examination using the gantry 2 but not an operation concerning the carrying or stop of the gantry 2. For example, an operation of urgently stopping the carrying of the gantry 2 is not inhibited. During the carrying of the gantry 2, preferably, a warning screen display or alarm sound representing that the gantry is moving is output onto the consoles 3 and 6 or a user navigation system (not shown) to notify the operator. Note that if safety is ensured in the examination rooms R1 and R2 (for example, there is neither unnecessary exposure nor the possibility of collision with the gantry), operation control from the consoles 3 and 6 may be canceled by the operator. During this time, tube warm-up, calibration, gantry rotation, and the like may be executed to improve examination throughput. In addition, to improve the examination throughput, the couches 4 and 7 may be allowed to be independently used concerning a function that does not need switching control of the moving direction according to the movement of the gantry 2, such as a function for subject setting (limited to vertical movement of the couch).

Next, the gantry control circuitry 28 determines whether sensor information based on the output signal of the sensor s1_2 between the examination rooms R1 and R2 is updated or not (step ST4). If NO in step ST4, the gantry control circuitry 28 determines whether it is within the time limit for the movement (step ST5). If it is within the time limit, the processes of steps ST2 to ST4 are continued. If it is outside the time limit, an error is detected (step ST6), the sensor information is updated from, for example, a setting from the CT console 3 (step ST7), and the processing from step ST1 is re-executed. Note that step ST4 may be processing of detecting update of the sensor information using a detection result of the sensor s1_2 as a trigger.

On the other hand, if it is determined in step ST4 that the sensor information is updated, the gantry control circuitry 28 executes movement control after the carrying and switching control of UI display based on the updated sensor information and the contents stored in the memory (step ST8). In this case, movement control and UI display in the examination room R1 are switched to movement control and UI display in the examination room R2. More specifically, for example, as shown in FIG. 7, couch top slide control in the reference direction is switched to self-propelled gantry control in the opposite direction, and tilt movement control in the reference direction is switched to tilt movement control in the opposite direction. Accordingly, for example, as shown in FIG. 4, UI display in the examination room R1 is switched to UI display in the examination room R2. In FIG. 4, the positive/negative display portion of the tilt moving amount is ±0°. Switching is done such that in the examination room R2, the tilt moving amount is displayed as negative (−) by the pressing operation of the first tilt movement button bt1, and the tilt moving amount is displayed as positive (+) by the pressing operation of the second tilt movement button bt2. Similarly, the positive/negative display portion of the moving amount in the moving direction is ±0 mm. Switching is done such that in the examination room R2, the gantry moving amount is displayed as positive (+) by the pressing operation of the first movement button bc1, and the gantry moving amount is displayed as negative (−) by the pressing operation of the second movement button bc2. Note that step ST8 may be executed using the detection result of the sensor s1_2 as a trigger. In addition, step ST8 may be executed not during the carrying of the gantry 2 but after the carrying of the gantry 2. At any rate, UI display is switched in accordance with the room where the gantry 2 is arranged after the carrying of the gantry 2.

Next, the gantry control circuitry 28 controls the carrier apparatus 27 to move the gantry to the initial position at the carrying destination. Under the control of the gantry control circuitry 28, the carrier apparatus 27 moves the gantry 2 to the initial position (step ST9).

On the other hand, in the X-ray console 6 in the examination room R2, the system control circuitry 66 determines, based on the output signal from the initial position detection sensor s2_2, whether the gantry 2 has reached the initial position (step ST10). If NO in step ST10, the gantry control circuitry 28 determines whether it is within the time limit for the movement (step ST11). If it is within the time limit, the processes of steps ST9 to ST11 are continued. If it is outside the time limit, the process returns to step ST6. Note that the determination of step ST10 may be executed by the gantry control circuitry 28.

If it is determined in step ST10 that the gantry 2 has reached the initial position, in the X-ray console 6, the system control circuitry 66 notifies the gantry 2 of the completion of the gantry movement (step ST12). Accordingly, in the gantry 2, the gantry control circuitry 28 stops the carrier apparatus 27.

After that, the gantry control circuitry 28 confirms the ID of the current position (step ST13). More specifically, the gantry control circuitry 28 determines whether the sensor information held in the memory as an examination room ID matches an examination room ID received from the X-ray console 6 in the examination room R2 (step ST14). If NO in step ST14, an error is detected (step ST15). To reacquire the current position, for example, the gantry 2 moves over the sensor s1_2 again to update the sensor information (step ST16). After that, the processing from step ST1 is re-executed. Alternatively, if an error is detected in step ST15, depending on a condition that, for example, the gantry has reached the correct initial position, and safety is ensured, forcible error reset (forcible setting) may be executed from the X-ray console 6 by the operation of the operator, and the process may then advance to step ST18.

On the other hand, if it is determined in step ST14 that the IDs match, the gantry control circuitry 28 permits the operation of the operator from the operation panels PL and PR and the X-ray console 6 (step ST18). At this time, the gantry control circuitry 28 may output a movement report message including the operation permission to the X-ray console 6 and thus display the message on the display 64 of the X-ray console 6.

In the examination room R2, the examination of the subject P by the X-ray angio-CT apparatus using the gantry 2 can be executed by the operation of the operator on the X-ray console 6 and the operation panels PL and PR. For example, the gantry control circuitry 28 controls the direction of the tilt movement of the gantry 2 in accordance with the examination room R2 where the gantry 2 is arranged during generation of a tilt movement command by the operation unit 28a. Alternatively, the gantry control circuitry 28 controls the direction of the relative movement of the gantry 2 and the couch 7 in accordance with the examination room R2 where the gantry 2 is arranged during generation of a movement command for a certain direction to the gantry 2 or the couch 7 by the operation unit 28a.

Even in a case in which the gantry 2 is moved from the examination room R2 to the examination room R1 after the examination in the examination room R2, the processes of steps ST1 to ST18 can be executed in a similar manner by appropriately replacing the corresponding constituent elements between the examination rooms R1 and R2, as is apparent. In the examination room R1 as well, the gantry control circuitry 28 can control the direction of the tilt movement or the direction of the relative movement in accordance with the examination room R1 where the gantry 2 is arranged during generation of a movement command by the operation unit 28a.

As described above, according to this embodiment, during generation of a command signal by the operation unit, the direction of the tilt movement of the gantry is controlled in accordance with the room where the gantry is arranged. Alternatively, during generation of a command signal by the operation unit, the direction of the relative movement of the gantry and the first couch or the second couch is controlled in accordance with the room where the gantry is arranged. It is therefore possible to prevent an operation error in the operation unit of the gantry.

At this time, at least one display of the positive/negative display of the direction of the tilt movement and the positive/negative display of the moving amount of the tilt movement provided on the operation unit may be switched in accordance with the room where the gantry is arranged. Alternatively, at least one display of the positive/negative display of the direction of the relative movement and the positive/negative display of the moving amount of the relative movement provided on the operation unit may be switched in accordance with the room where the gantry is arranged. This can prevent a mismatch in the UI display of the gantry.

In addition, the direction of the tilt movement corresponding to the room to which the gantry is carried may be switched using a detection result of the gantry detector as a trigger, and during generation of the command signal, the direction of the tilt movement of the gantry may be controlled based on the switched direction. Alternatively, the direction of the relative movement corresponding to the room to which the gantry is carried may be switched using a detection result of the gantry detector as a trigger, and during generation of the command signal, the direction of the relative movement may be controlled based on the switched direction. This can prevent a mismatch in the movement control of the gantry.

For a supplement, movement control of the gantry or UI display on the operation panel is conventionally fixed in a multi-room solution. In this embodiment, however, a plurality of patterns of movement control or UI display are prepared, and the patterns are switched in accordance with the carrying destination of the gantry or the orientation of the gantry after the carrying. It is therefore possible to eliminate a mismatch between the shared gantry and a plurality of system combinations or couch positions.

According to this embodiment, control is automatically switched based on sensor information, and a movement report can be explicitly presented to the operator. Hence, the operator can safely handle the gantry without a sense of discomfort.

According to this embodiment, the memory of the gantry control circuitry 28 stores the room where the gantry 2 is arranged and the direction of the tilt movement in association, and stores the room where the gantry is arranged and the direction of the relative movement in association. Accordingly, since the gantry control circuitry 28 controls the direction of the tilt movement or the direction of the relative movement based on the contents stored in the memory, the contents of switching control can easily be set in the memory.

According to this embodiment, when the switching function sc of executing switching control is arranged in the gantry 2, the switching function sc of the X-ray CT system can be concentrated to one point.

According to this embodiment, when the switching function sc is arranged in each console, the arrangements of the consoles concerning switching control can be standardized. For a supplement, instead of providing the consoles with different switching functions sc specialized to the consoles in accordance with the orientation of the gantry 2 and the like, a common switching function sc is provided in the consoles. It is therefore possible to standardize the arrangements of the consoles concerning switching control.

According to this embodiment, the gantry detector such as a sensor detects that the gantry 2 is being carried to the carrying destination, and the switching function sc executes switching control using the detection result as a trigger. It is therefore possible to easily set the position of the gantry 2 that generates the trigger for switching control.

According to this embodiment, a plurality of sensors are arranged between the couches and detect the gantry 2 that is being carried. It is therefore possible to easily set the position of the gantry 2 that generates the trigger for switching control independently of whether the couches exist in different examination rooms or in the same examination room.

Second Embodiment

Figure 10:
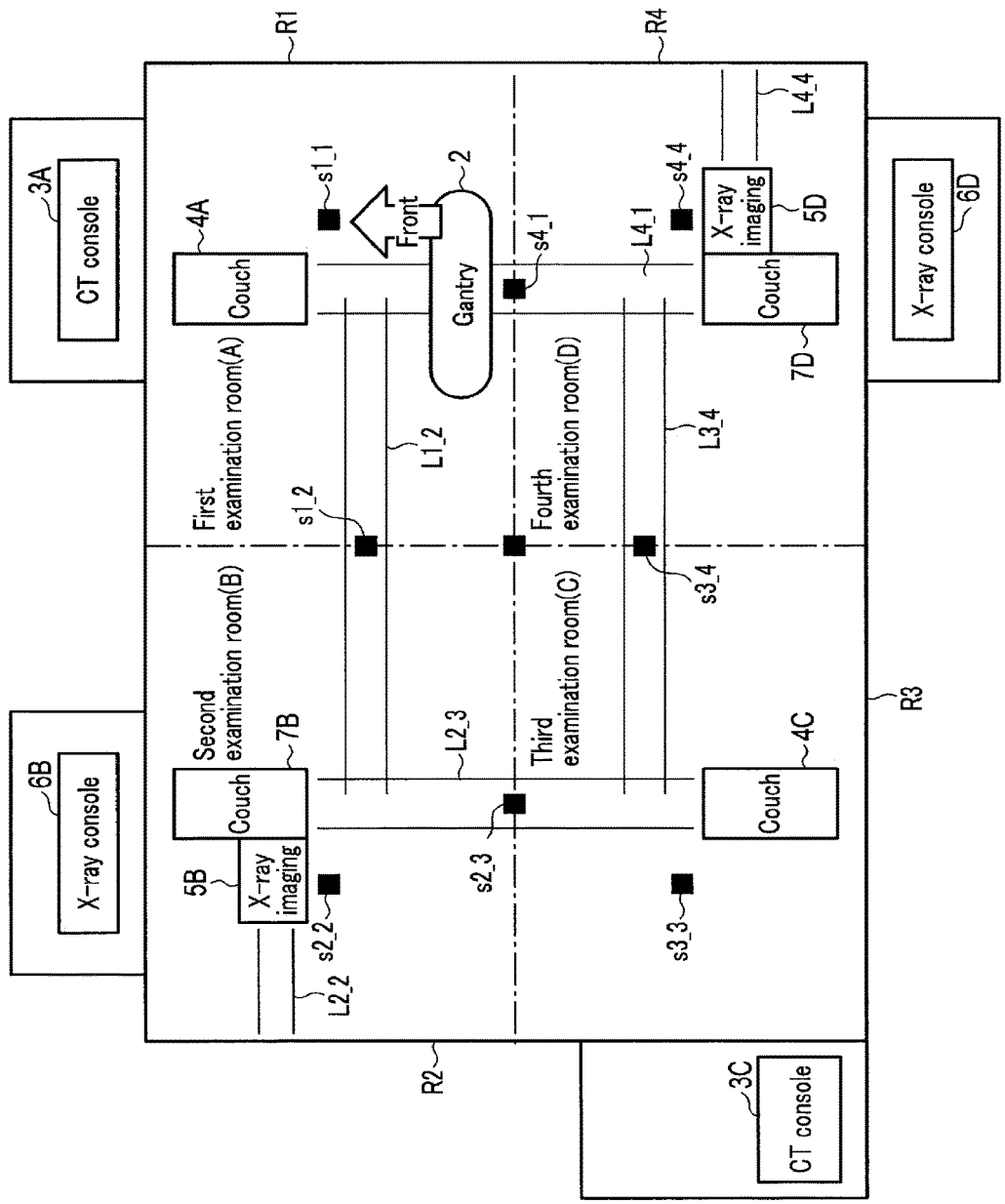
FIG. 10 is a schematic view showing a layout arrangement in a case in which an X-ray CT system according to the second embodiment is applied to a 4-room solution.
Figure 11:
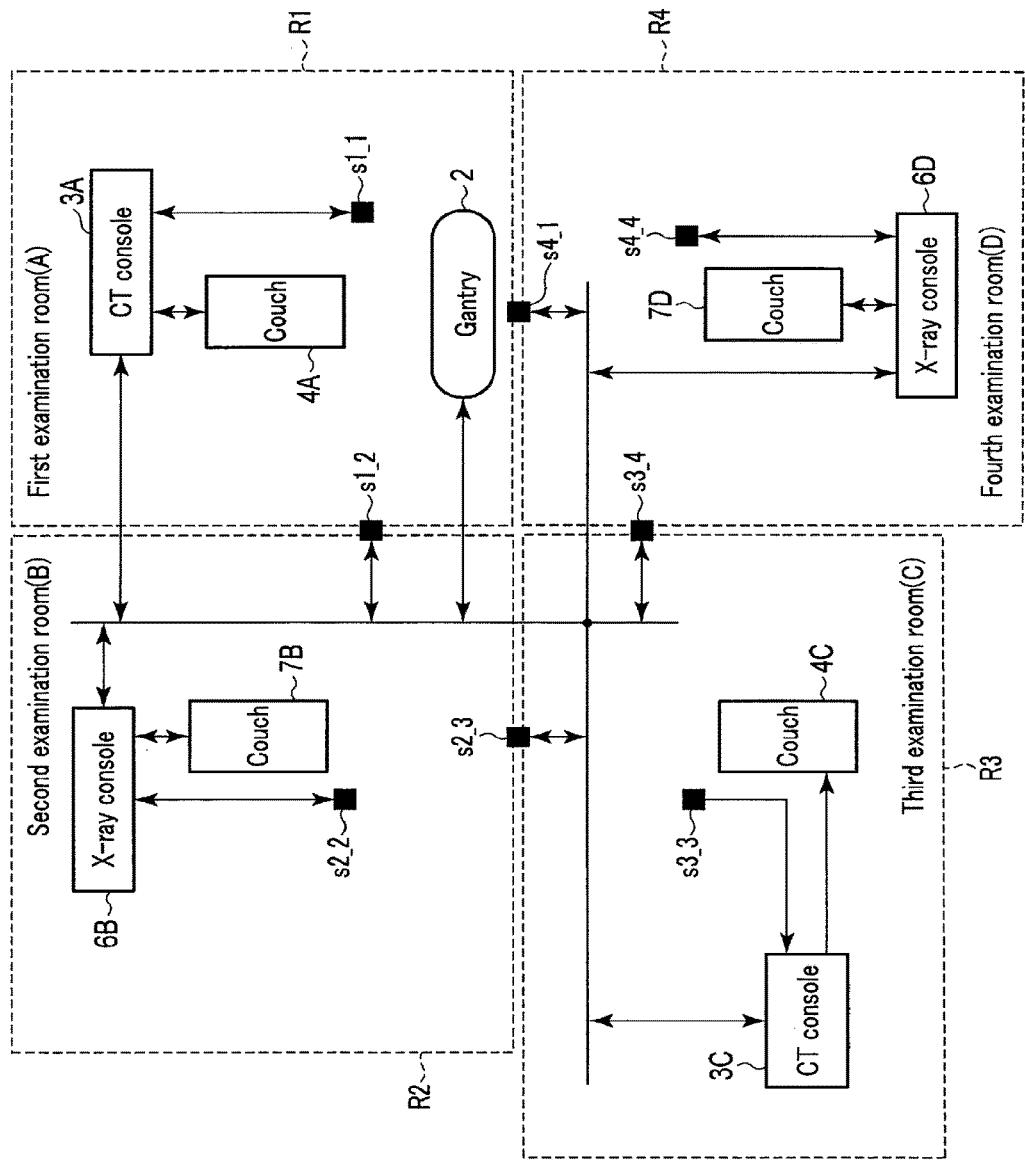
FIG. 11 is a schematic view showing the network configuration of the X-ray CT system shown in FIG. 10.

FIG. 10 is a schematic view showing a layout arrangement in a case in which an X-ray CT system according to the second embodiment is applied to a 4-room solution. FIG. 11 is a schematic view showing the network configuration of the X-ray CT system shown in FIG. 10. The same reference numerals as in the above-described drawings denote almost the same parts, and a detailed description thereof will be omitted. Different parts will mainly be described here. In the following embodiments as well, a repetitive description will be omitted in a similar manner.

That is, in the second embodiment, the arrangement applied to a 2-room solution in the first embodiment is modified to an arrangement applied to a 4-room solution. Accordingly, the two examination rooms R1 and R2 are expanded to four rooms, that is, first to fourth examination rooms R1 to R4. More specifically, the examination rooms R1 and R2 according to the embodiment correspond to the first examination room (A) R1 and the fourth examination room (D) R4 according to the second embodiment. The second examination room (B) R2 and the third examination room (C) R3 are newly added. The first to fourth examination rooms R1 to R4 are four rooms divided by, for example, almost cross-shaped partition walls. Defining the first examination room R1 as a reference, the second examination room R2, the third examination room R3, and the fourth examination room R4 are sequentially arranged counterclockwise viewed from above. However, the arrangement of the four rooms is not limited to this, and an arbitrary arrangement such as an almost L-shaped or almost T-shaped arrangement can be applied.

As shown in FIG. 10, in the first examination room (A) R1, a CT console 3A, a couch 4A, and an initial position detection sensor s1_1 are arranged as an X-ray CT apparatus that shares a gantry 2. The CT console 3A, the couch 4A, and the sensor s1_1 have the same arrangements as the CT console 3, the couch 4, and the sensor s1_1 shown in FIG. 3.

In the second examination room (B) R2, an X-ray imaging apparatus 5B, an X-ray console 6B, a couch 7B, an initial position detection sensor s2_2, and rails L2_2 provided on the ceiling are arranged as an X-ray angio-CT apparatus that shares the gantry 2. The X-ray imaging apparatus 5B, the X-ray console 6B, the couch 7B, the sensor s2_2, and the rails L2_2 have the same arrangements as the X-ray imaging apparatus 5, the X-ray console 6, the couch 7, the sensor s2_2, and the rails L2_2 shown in FIGS. 2 and 3.

In the third examination room (C) R3, a CT console 3C, a couch 4C, and an initial position detection sensor s3_3 are arranged as an X-ray CT apparatus that shares the gantry 2. The CT console 3C, the couch 4C, and the sensor s3_3 have the same arrangements as the CT console 3, the couch 4, and the sensor s1_1 shown in FIG. 3.

In the fourth examination room (D) R4, an X-ray imaging apparatus 5D, an X-ray console 6D, a couch 7D, an initial position detection sensor s4_4, and rails L4_4 provided on the ceiling are arranged as an X-ray angio-CT apparatus that shares the gantry 2. The X-ray imaging apparatus 5D, the X-ray console 6D, the couch 7D, the sensor s4_4, and the rails L4_4 have the same arrangements as the X-ray imaging apparatus 5, the X-ray console 6, the couch 7, the sensor s2_2, and the rails L2_2 shown in FIGS. 2 and 3.

Carrying rails L1_2 are laid between the initial position near the couch 4A in the first examination room (A) R1 and the initial position near the couch 7B in the second examination room (B) R2. An opening/closing door 9 (not shown) and a sensor s1_2 are arranged at the boundary between the first examination room (A) R1 and the second examination room (B) R2. The gantry 2 is carried on the carrying rails L1_2 in the lateral direction from a state in which the front surface faces the couch 4A. For this reason, the front surface of the gantry 2 faces the couch 7B.

Carrying rails L2_3 are laid between the initial position near the couch 7B in the second examination room (B) R2 and the initial position near the couch 4C in the third examination room (C) R3. The opening/closing door 9 (not shown) and a sensor s2_3 are arranged at the boundary between the second examination room (B) R2 and the third examination room (C) R3. The gantry 2 is carried on the carrying rails L2_3 in the back direction from a state in which the front surface faces the couch 7B. For this reason, the back surface of the gantry 2 faces the couch 4C.

Carrying rails L3_4 are laid between the initial position near the couch 4C in the third examination room (C) R3 and the initial position near the couch 7D in the fourth examination room (D) R4. The opening/closing door 9 (not shown) and a sensor s3_4 are arranged at the boundary between the third examination room (C) R3 and the fourth examination room (D) R4. The gantry 2 is carried on the carrying rails L3_4 in the lateral direction from a state in which the back surface faces the couch 4C. For this reason, the back surface of the gantry 2 faces the couch 7D.

Carrying rails L4_1 are laid between the initial position near the couch 7D in the fourth examination room (D) R4 and the initial position near the couch 4A in the first examination room (A) R1. The opening/closing door 9 (not shown) and a sensor s4_1 are arranged at the boundary between the fourth examination room (D) R4 and the first examination room (A) R1. The gantry 2 is carried on the carrying rails L4_1 in the front direction from a state in which the back surface faces the couch 7D. For this reason, the front surface of the gantry 2 faces the couch 4A.

As shown in FIG. 11, the gantry 2, the CT consoles 3A and 3C, the X-ray consoles 6B and 6D, and the sensors s1_2, S2_3, S3_4, and S4_1 can communicate with each other via a network by, for example, CAN communication.

The CT console 3A can communicate with the couch 4A and the initial position detection sensor s1_1. The X-ray console 6B can communicate with the couch 7B and the initial position detection sensor s2_2. The CT console 3C can communicate with the couch 4C and the initial position detection sensor s3_3. The X-ray console 6D can communicate with the couch 7D and the initial position detection sensor s4_4. Note that the embodiment is not limited to this, and the couches 4A, 7B, 4C, and 7D and the initial position detection sensor s1_1, s2_2, s3_3, and s4_4 may also be communicable with the gantry 2 and the like via a network by, for example, CAN communication.

Figure 12:
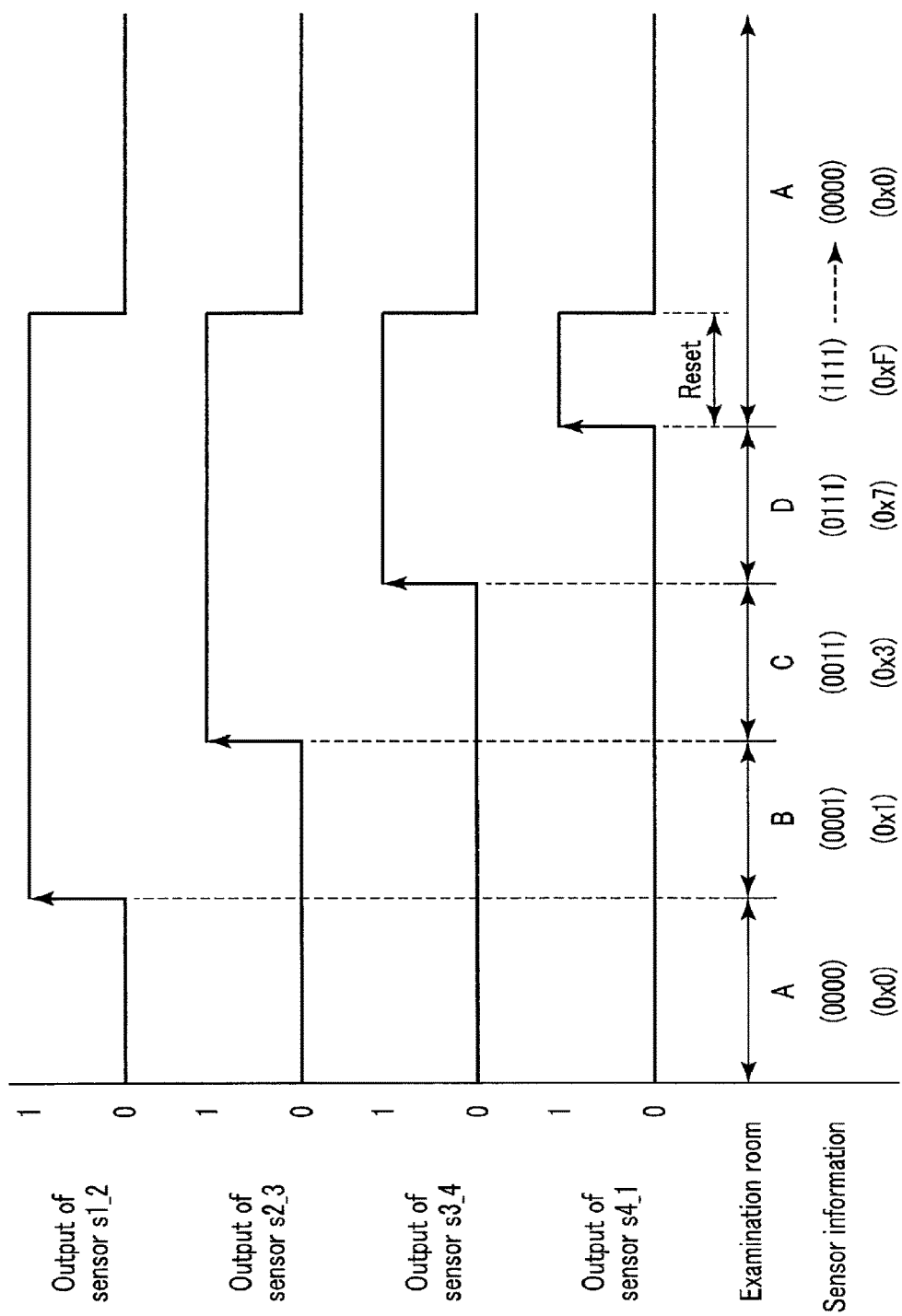
FIG. 12 is a schematic view showing a sensor output according to the embodiment.

Upon detecting the gantry 2 that is being carried, the four sensors s1_2, S2_3, S3_4, and S4_1 arranged at the boundaries between the examination rooms R1 to R4 each transmits an output signal "1" to a gantry control circuitry 28 in place of an output signal "0", as shown in FIG. 12. Note that the output signal "0" and the output signal "1" may be replaced.

The gantry control circuitry 28 holds the values of the output signal from the sensors s1_2, S2_3, S3_4, and S4_1 in a memory as sensor information. In this case, the sensor information has a 4-digit value (the value of the sensor S4_1, the value of the sensor S3_4, the value of the sensor S2_3, and the value of the sensor s1_2) generated by arranging the values from the sensors s1_2, S2_3, S3_4, and S4_1 in the digits. For example, a sensor number is assigned to each of the sensors s1_2, S2_3, S3_4, and S4_1, and the values of the output signals from the sensors s1_2, S2_3, S3_4, and S4_1 and the sensor numbers are output to the gantry control circuitry 28. The gantry control circuitry 28 updates the sensor information based on the values of the output signals and the sensor numbers. This makes it possible to easily manage the sensors s1_2, S2_3, S3_4, and S4_1 and the sensor information. Note that the arrangement of the digits in the sensor information is merely an example, and another arrangement may be employed. That is, the arrangement need not always estimate the position of the gantry 2 based on the order of ON-state transition of the plurality of sensors s1_2, S2_3, S3_4, and S4_1, and need only estimate the position of the gantry 2 in accordance with the combination of the values from the sensors s1_2, S2_3, S3_4, and S4_1. In addition, when the value of the sensor information reaches "1111", the gantry control circuitry 28 resets the sensor information in the memory and the sensors s1_2, S2_3, S3_4, and S4_1.

Additionally, the memory of the gantry control circuitry 28 may store the sensor information representing the values of the output signals of the sensors s_12, S2_3, S3_4, and S4_1, the orientation of the gantry 2 with respect to a couch, a couch, an examination room, and control information in association, as show in FIG. 13. At this time, the orientation of the gantry 2, the couch, the examination room, and the control information associated with the sensor information in advance can be read out based on the held sensor information. For the examination room (A) R1 corresponding to sensor information "0x0" (=0000), the control information represents couch top slide control in the reference direction and tilt movement control in the reference direction. For the examination room (B) R2 corresponding to sensor information "0x1" (=0001), the control information represents self-propelled gantry control in the reference direction and tilt movement control in the reference direction. For the examination room (C) R3 corresponding to sensor information "0x3" (=0011), the control information represents couch top slide control in the opposite direction and tilt movement control in the opposite direction. For the examination room (D) R4 corresponding to sensor information "0x7" (=0111), the control information represents self-propelled gantry control in the opposite direction and tilt movement control in the opposite direction.

According to the above-described arrangement, the same operations as in steps ST1 to ST18 described above are executed between the console in the examination room where the gantry 2 is located before carrying, the gantry 2, and the console in the examination room of the carrying destination.

Of steps ST1 to ST18, the operations of steps ST4 and ST8 will be described here in detail. In step ST4 of this embodiment, it is determined whether sensor information formed from the values of the output signals of the four sensors s1_2, S2_3, S3_4, and S4_1 is updated, unlike the first embodiment.

If it is determined in step ST4 that the sensor information is updated, the gantry control circuitry 28 executes movement control after the carrying and switching control of UI display based on the updated sensor information and the contents stored in the memory (step ST8).

In step ST8, every time the gantry 2 that is being carried is detected by the sensors s1_2, S2_3, S3_4, and S4_1, the gantry control circuitry 28 switches movement control and UI display. The gantry control circuitry 28 performs control by determining which examination room has the system combined with the gantry 2 that has moved and whether the UI display is not changed at that time.

For example, the X-ray CT apparatus in the examination room A is defined as a reference. In the examination room B, the gantry 2 is combined with the X-ray angio-CT apparatus. Hence, the gantry control circuitry 28 switches from couch top slide control to self-propelled gantry control. More specifically, when the gantry 2 is carried from the first examination room (A) R1 to the second examination room (B) R2, movement control and UI display in the first examination room (A) R1 are switched to movement control and UI display in the second examination room (B) R2. More specifically, for example, as shown in FIG. 13, couch top slide control in the reference direction is switched to self-propelled gantry control in the opposite direction. Tilt movement control in the reference direction remains unchanged even in the second examination room (B) R2.

Accordingly, UI display in the first examination room (A) R1 is switched to UI display in the second examination room (B) R2. Although the UI display is not illustrated, the approaching direction, the separating direction, and the tilting direction in the first examination room (A) R1 and the second examination room (B) R2 are the same as those on the left side (R1 side) of FIG. 5. This is because the directions in the examination room R1 shown in FIG. 5 correspond to the directions in the first examination room (A) R1 and the second examination room (B) R2 according to the second embodiment, respectively.

In the examination room C, since the gantry 2 faces the opposite side, the gantry control circuitry 28 reverses the couch top slide direction and the tilt movement direction. For example, in step ST8, when carrying the gantry 2 from the second examination room (B) R2 to the third examination room (C) R3, movement control and UI display in the second examination room (B) R2 are switched to movement control and UI display in the third examination room (C) R3. More specifically, for example, as shown in FIG. 13, self-propelled gantry control in the reference direction is switched to couch top slide control in the opposite direction. Tilt movement control in the reference direction is switched to tilt movement control in the opposite direction. Accordingly, UI display in the second examination room (B) R2 is switched to UI display in the third examination room (C) R3. Although the UI display is not illustrated, the approaching direction, the separating direction, and the tilting direction in the second examination room (B) R2 and the third examination room (C) R3 are the same as in FIG. 5. This is because the directions in the examination room R1 shown in FIG. 5 correspond to the directions in the second examination room (B) R2, and the directions in the examination room R2 shown in FIG. 5 correspond to the directions in the third examination room (C) R3.

In the examination room D, the gantry control circuitry 28 performs switching to self-propelled gantry control and reverses the tilt movement direction. For example, in step ST8, when carrying the gantry 2 from the third examination room (C) R3 to the fourth examination room (D) R4, movement control and UI display in the third examination room (C) R3 are switched to movement control and UI display in the fourth examination room (D) R4. More specifically, for example, as shown in FIG. 13, couch top slide control in the opposite direction is switched to self-propelled gantry control in the opposite direction. Tilt movement control in the opposite direction remains unchanged even in the fourth examination room (D) R4. Accordingly, UI display in the third examination room (C) R3 is switched to UI display in the fourth examination room (D) R4. Although the UI display is not illustrated, the approaching direction, the separating direction, and the tilting direction in the third examination room (C) R3 and the fourth examination room (D) R4 are the same as those on the right side (R2 side) of FIG. 5. This is because the directions in the examination room R2 shown in FIG. 5 correspond to the directions in the third examination room (C) R3 and the fourth examination room (D) R4 according to the second embodiment, respectively.

The operations of steps ST4 and ST8 have been described above.

Such an X-ray CT system executes the operations of steps ST1 to ST18 shown in FIG. 9 so as to include the operations of steps ST4 and ST8 described above every time the gantry 2 moves to another examination room.

As described above, according to this embodiment, even if the X-ray CT system is applied to the 4-room solution, the same effects as in the first embodiment can be obtained.

Note that the second embodiment may be modified to the first to fourth modifications to be described below. That is, the method of estimating the position of the gantry 2 is not limited to the method based on the sensor information from the sensors s1_2, S2_3, S3_4, and S4_1 arranged at the boundaries of the examination rooms, and may be based on the following first to fourth modifications or modifications thereof. For a supplement, in the first to fourth modifications, the sensors s1_2, S2_3, S3_4, and S4_1 and sensor information are not used. In the first to fourth modifications, the initial position detection sensor s1_1 to s4_4 (not shown) or an alternate means thereof is used. As the alternate means, for example, a means for detecting that a carrier apparatus 27 for carrying the gantry 2 has reached the initial position by providing an encoder in the carrier apparatus 27 and detecting the moving amount of the carrier apparatus 27 can appropriately be used.

The first modification will be direction first. The first modification is an example concerning a mechanical switch.

Figure 14:
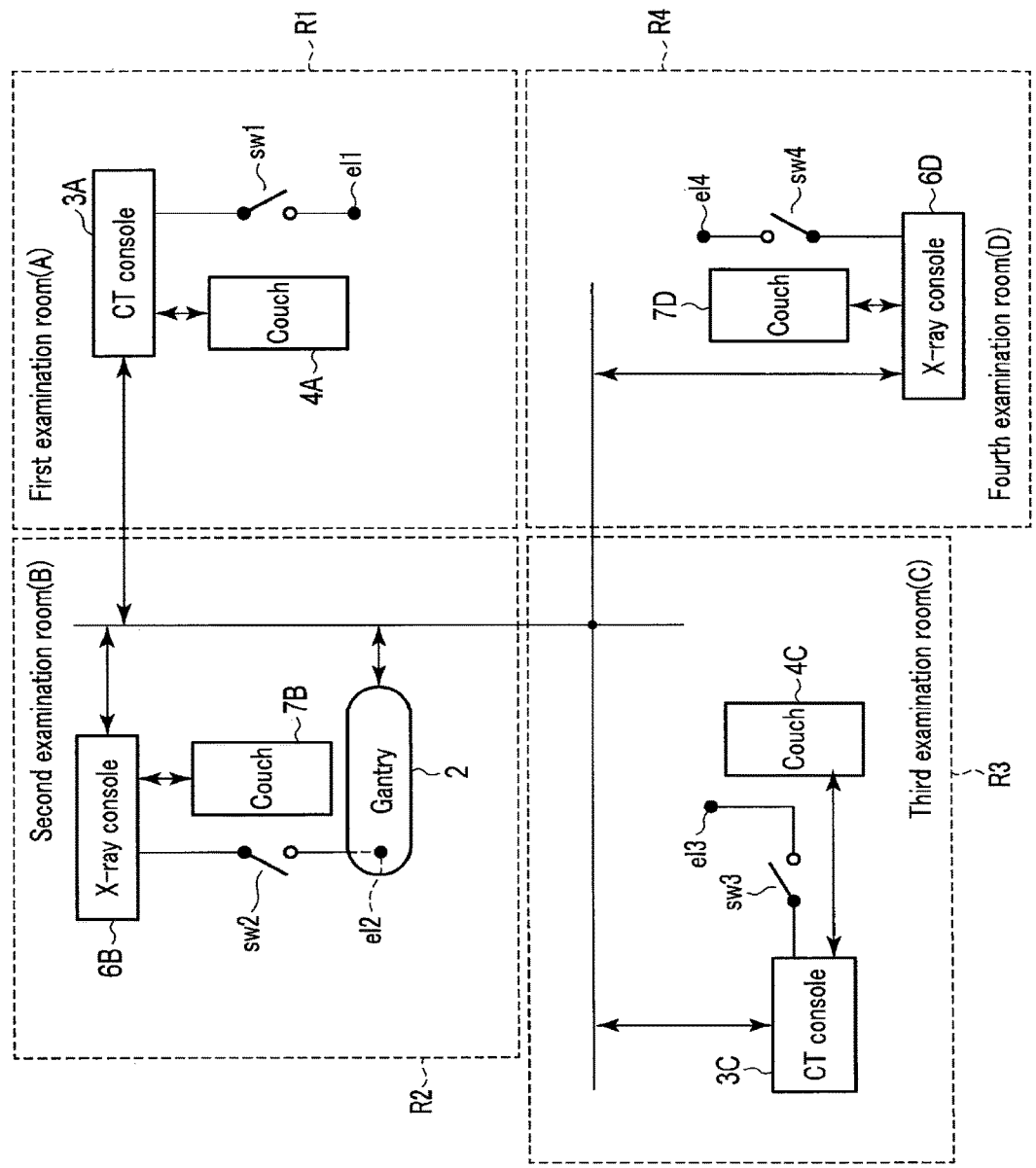
FIG. 14 is a schematic view showing the schematic arrangement of the first modification of the embodiment.

That is, as shown in FIG. 14, the first modification includes mechanical switches sw1 to sw4 as first to fourth switches arranged near the couches 4A, 7B, 4C, and 7D, respectively, and configured to switch the connection between the gantry 2 arranged in one of the first to fourth examination rooms R1 to R4 and the consoles 3A, 6B, 3C, and 6D for the gantry 2 to an OFF state or an ON state. Each of the mechanical switches sw1 to sw4 has one terminal electrically connected to a corresponding one of the consoles 3A, 6B, 3C, and 6D and the other terminal electrically connected to a corresponding one of electrodes el1 to el4 arranged near the couches. The electrodes el1 to el4 are arranged, for example, on both end sides of the carrying rails L1_2 and L3_4 and each have a long shape to connect an end side and the initial position. For example, as shown in FIG. 14, if the gantry 2 reaches the vicinity of the couch 7B, the electrode el12 arranged near the couch 7B contacts an electrode (not shown) of the gantry 2 and electrically connects the gantry 2 to the mechanical switch sw2. If the mechanical switch sw2 is turned on, the gantry 2 and the X-ray console 6B are electrically connected. For example, assume that a current is output from the X-ray console 6B to the mechanical switch sw2 via a reference power supply and a reference resistor, and supplied to the gantry 2 via the mechanical switch sw2. The reference resistor has a resistance value that changes between the consoles. Next, assume that the current flows to the ground side via a predetermined resistor in the gantry 2. In the gantry 2, the voltage value across the predetermined resistor is measured, thereby acquiring an eigenvalue (voltage value) for each carrying destination in place of sensor information. That is, the eigenvalue is set in the memory of the gantry control circuitry 28 in place of the sensor information shown in FIG. 13. Hence, both the gantry 2 and the X-ray console 6B can determine, by the ON state of the mechanical switch sw2, that the gantry 2 has reached the vicinity of the couch 7B of the carrying destination. The remaining electrodes el1, el3, and el4 function in the same way as described above.

Figure 15:
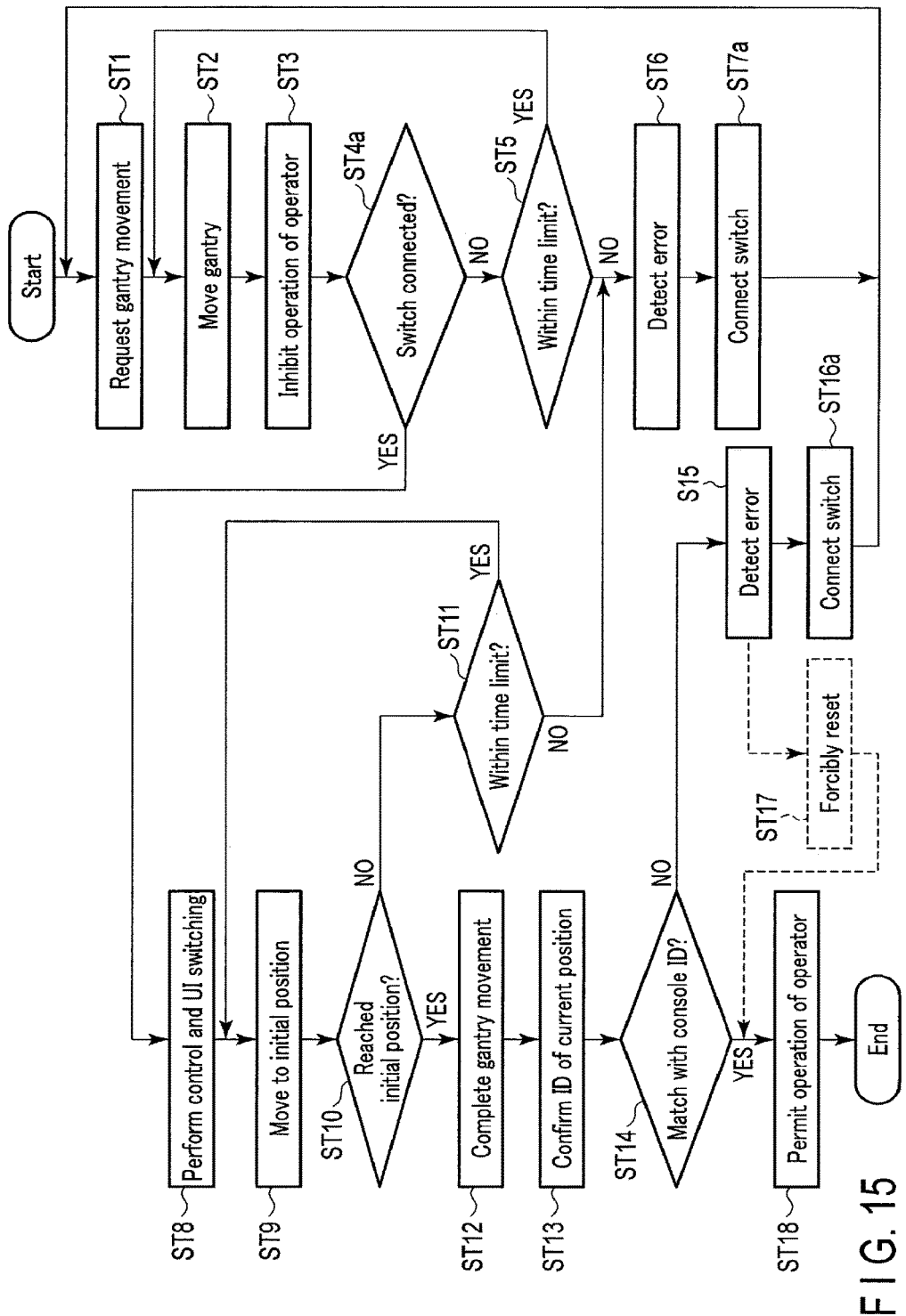
FIG. 15 is a flowchart for explaining the operation according to the first modification of the embodiment.

Hence, for example, as shown in FIG. 15, steps ST1 to ST3, ST5, ST6, ST8 to ST15, ST17, and ST18 irrelevant to the above-described sensors s1_2, S2_3, S3_4, and S4_1 are executed, as described above. Steps ST4, ST7, and ST16 concerning the sensors s1_2, s2_3, s3_4, and s4_1 are executed as shown in steps ST4a, ST7a, and ST16a.

Step ST4*a* will be described first. Steps ST1 (gantry moving request) to ST3 (inhibition of operations concerning CT examination) are executed. During the carrying of the gantry 2, the gantry control circuitry 28 determines whether the mechanical switch sw2 is connected (step ST4*a*). If NO in step ST4*a*, the processes of steps ST2 to ST5 are repetitively executed within the time limit (YES in step ST5), as described above. Assume that the gantry 2 has reached the vicinity of the couch 7B of the carrying destination. At this time, the gantry 2 stops moving by, for example, an operation on an operation unit 28*a*. In addition, the electrode el2 arranged near the couch 7B electrically connects the gantry 2 to the mechanical switch sw2 via the electrode (not shown) of the gantry 2. Next, when the operator turns on the mechanical switch sw2, the gantry control circuitry 28 determines in step ST4*a* that the mechanical switch sw2 is connected. From then on, the processing from step ST8 is executed in a similar manner.

Step ST7*a* will be described. If the determination of step ST4*a* results in NO, and it is outside the time limit (NO in step ST5), an error is detected (step ST6). After that, for example, the gantry 2 is notified of a state in which the mechanical switch sw1 of the carrying source is connected by a setting from the CT console 3 (step ST7*a*), and the processing from step ST1 is re-executed.

Step ST16*a* will be described. If the determination of step ST14 results in NO, an error is detected (step ST15). After that, to reacquire the current position, for example, the mechanical switch sw2 of the carrying destination is connected again to update the connection state (step ST16*a*). After that, the processing from step ST1 is re-executed.

According to the first modification, even if the sensors s1_2, S2_3, S3_4, and S4_1 at the boundaries of the examination rooms and the sensor information of them are omitted, the same effects as in the above-described embodiments can be obtained by the arrangement that connects the gantry 2 and the console of the carrying destination by a mechanical switch. For easier understanding, a description will be made here with focus on the two examination rooms R1 and R2. For example, when the gantry 2 is connected to the first console (3A) or the second console (6B) via the first switch (sw1) or the second switch (sw2), the control circuitry detects the room (R1 or R2) where the gantry 2 is arranged. Even when such a detection method is used, the control circuitry can control the direction of the tilt movement or the direction of the relative movement in accordance with the room where the gantry 2 is arranged.

The second modification will be described next. The second modification is an example concerning physical switching of a connecting cable between the gantry 2 and each console in a case in which there are a plurality of scanning consoles.

Figure 16:
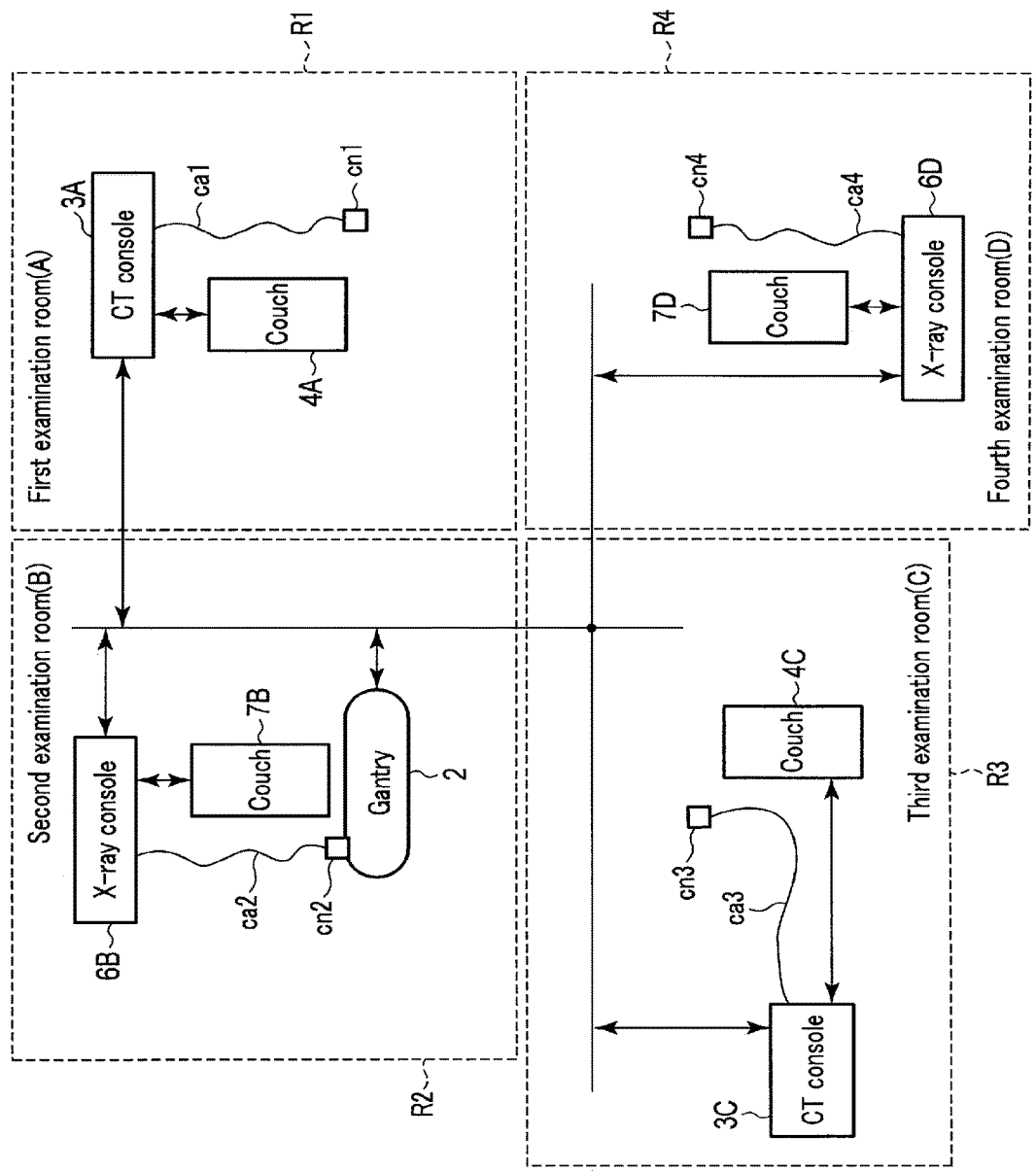
FIG. 16 is a schematic view showing the schematic arrangement of the second modification of the embodiment.

More specifically, as shown in FIG. 16, the second modification includes first to fourth cables ca1 to ca4 arranged in the first to fourth examination rooms R1 to R4, respectively, and extended from the first to fourth consoles 3A, 6B, 3C, and 6D for the gantry 2, respectively, and first to fourth connectors cn1 to cn4 provided at the distal ends of the first to fourth cables ca1 to ca4, respectively, and connectable to the gantry 2. More specifically, each of the cables ca1 to ca4 has one end connected to a corresponding one of the consoles 3A, 6B, 3C, and 6D and has a corresponding one of the connectors cn1 to cn4 at the other end. If the gantry 2 reaches the vicinity of the couch, the connectors cn1 to cn4 are each connected to a connector (not shown) of the gantry 2 and electrically connect the gantry 2 to the consoles 3A, 6B, 3C, and 6D. In a case in which the connector cn2 is connected to the gantry 2, the second modification functions in the same way as in a case in which the mechanical switch sw2 according to the first modification is turned on.

For this reason, in the second modification, the gantry 2 connected to (a cable via) a connector can acquire an eigenvalue (voltage value) for each carrying destination in place of sensor information, as in the first modification. That is, the eigenvalue is set in the memory of the gantry control circuitry 28 in place of the sensor information shown in FIG. 13. Hence, both the gantry 2 and the X-ray console 6B can determine, by the connection of (a cable via) the connector cn2, that the gantry 2 has reached the vicinity of the couch 7B of the carrying destination. The remaining connectors cn1, cn3, and cn4 function in the same way as described above.

Figure 17:
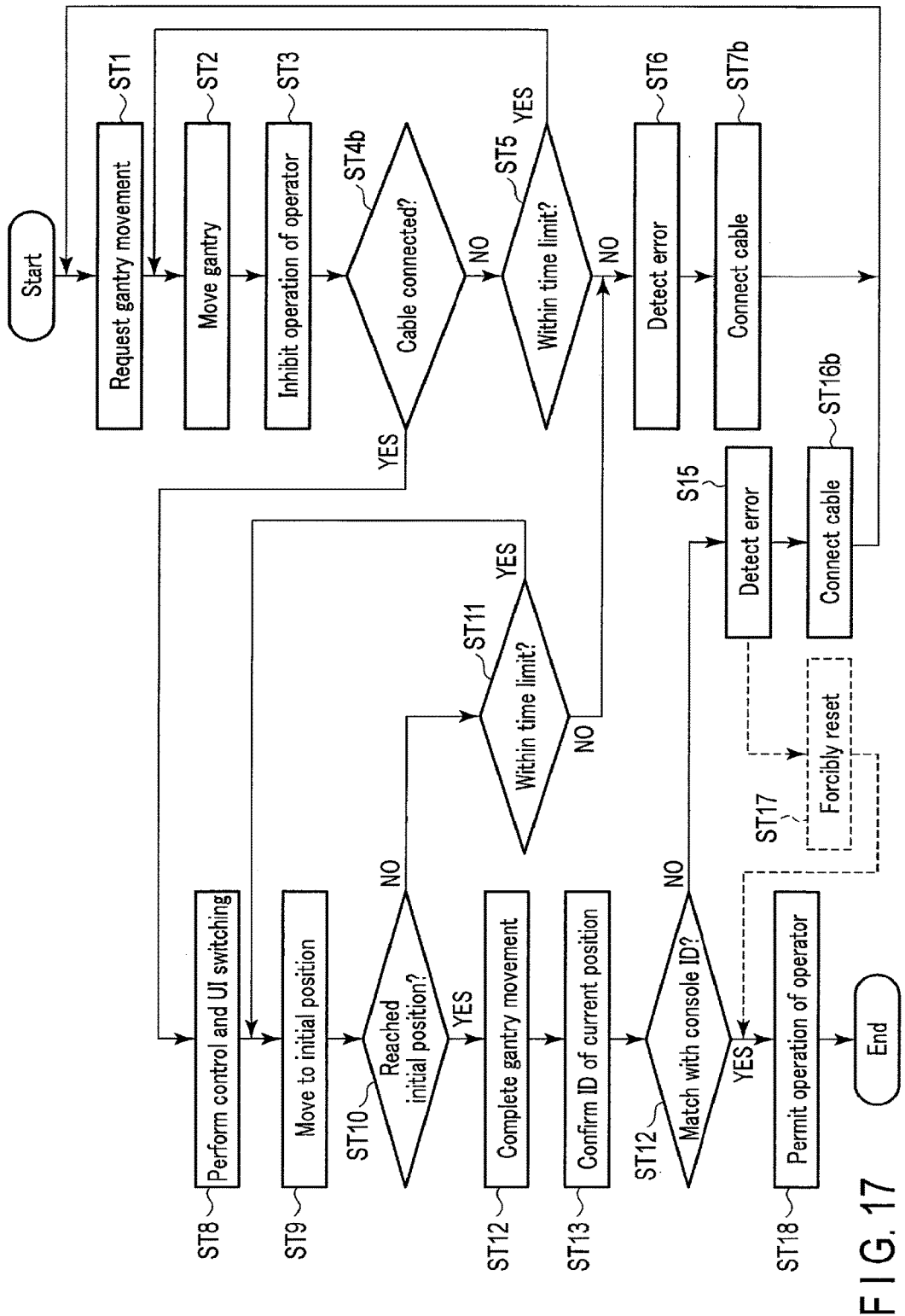
FIG. 17 is a flowchart for explaining the operation according to the second modification of the embodiment.

Hence, for example, as shown in FIG. 17, steps ST1 to ST3, ST5, ST6, ST8 to ST15, ST17, and ST18 irrelevant to the above-described sensors s1_2, S2_3, S3_4, and S4_1 are executed, as described above. Steps ST4, ST7, and ST16 concerning the sensors s1_2, s2_3, s3_4, and s4_1 are executed as shown in steps ST4*b*, ST7*b*, and ST16*b*.

Step ST4*b* will be described first. Steps ST1 (gantry moving request) to ST3 (inhibition of operations concerning CT examination) are executed. During the carrying of the gantry 2, the gantry control circuitry 28 determines whether the cable ca2 is connected via the connector cn2 (step ST4*b*). If NO in step ST4*b*, the processes of steps ST2 to ST5 are repetitively executed within the time limit (YES in step ST5), as described above. Assume that the gantry 2 has reached the vicinity of the couch 7B of the carrying destination. At this time, the gantry 2 stops moving by, for example, an operation on the operation unit 28*a*. In addition, the cable ca2 connected to the X-ray console 6B electrically connects the gantry 2 to the X-ray console 6B when the connector cn2 at the distal end is connected to the connector (not shown) of the gantry 2. Accordingly, the gantry control circuitry 28 determines in step ST4*b* that the gantry 2 is connected of the connector cn2 of the X-ray console 6B. From then on, the processing from step ST8 is executed in a similar manner.

Step ST7*b* will be described. If the determination of step ST4*b* results in NO, and it is outside the time limit (NO in step ST5), an error is detected (step ST6). After that, for example, the gantry 2 is notified of a state in which the cable ca1 of the carrying source is connected by a setting from the CT console 3 (step ST7*b*), and the processing from step ST1 is re-executed.

Step ST16*b* will be described. If the determination of step ST14 results in NO, an error is detected (step ST15). After that, to reacquire the current position, for example, the cable ca2 of the carrying destination is connected again to update the connection state (step ST16*b*). After that, the processing from step ST1 is re-executed.

According to the second modification, even if the sensors s1_2, S2_3, S3_4, and S4_1 at the boundaries of the examination rooms and the sensor information of them are omitted, the same effects as in the above-described embodiments and the first modification can be obtained by the arrangement that connects the gantry 2 and the console of the carrying destination by a cable. For easier understanding, a description will be made here with focus on the two examination rooms R1 and R2. For example, when the gantry 2 is connected to the first console (3A) or the second console (6B) via the first connector (cn1) or the second connector (cn2), the control circuitry detects the room (R1 or R2) where the gantry 2 is arranged. Even when such a detection method is used, the control circuitry can control the direction of the tilt movement or the direction of the relative movement in accordance with the room where the gantry 2 is arranged.

The third modification will be described next. The third modification is directed to switching by determination of the spatial distance (whether within a communication range or not) between a console (or an examination room) and the gantry 2 by wireless communication.

Figure 18:
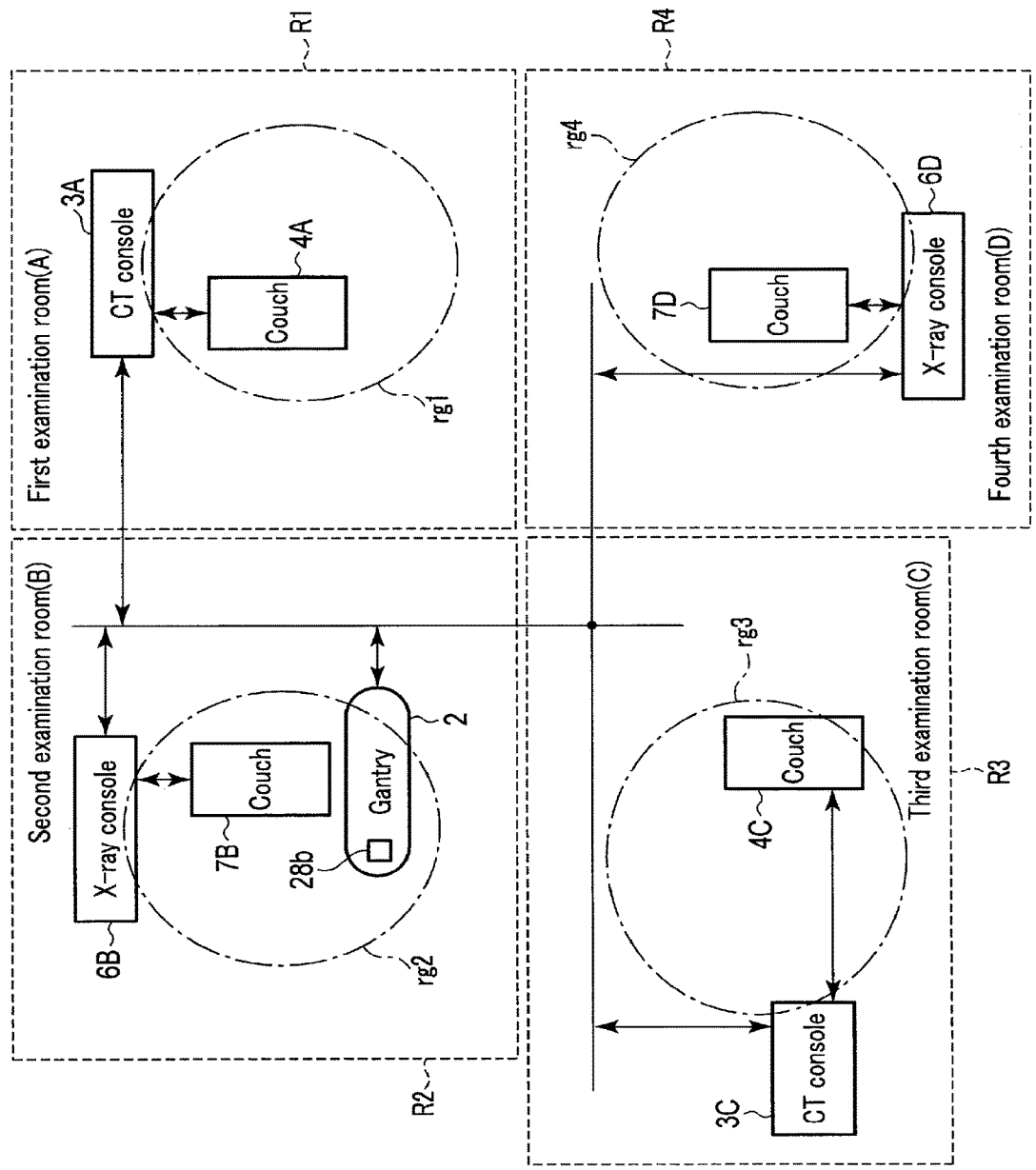
FIG. 18 is a schematic view showing the schematic arrangement of the third modification of the embodiment.

More specifically, as shown in FIG. 18, the third modification includes first to fourth pieces of wireless communication circuitry configured to cause pieces of communication interface circuitry 34 and 63 of the consoles 3A, 6B, 3C, and 6D arranged in the examination rooms R1, R2, R3, and R4 to transmit radio signals within communication ranges rg1, rg2, rg3, and rg4 near the couches. The gantry 2 includes 0th wireless communication circuitry 28$b$ configured to receive the radio signals within the communication ranges rg1, rg2, rg3, and rg4. That is, the 0th wireless communication circuitry 28$b$ can perform wireless communication with the first to fourth pieces of wireless communication circuitry when located in the communication ranges rg1, rg2, rg3, and rg4. The wireless communication circuitry 28$b$ is connected to the gantry control circuitry 28.

If the gantry 2 reaches the communication ranges rg1, rg2, rg3, and rg4 near the couches, the wireless communication circuitry 28$b$ in the gantry 2 receives the radio signals in the communication ranges rg1, rg2, rg3, and rg4 and can perform wireless communication with the consoles 3A, 6B, 3C, and 6D. The third modification functions in the same way as, for example, in a case in which the connector cn2 is connected to the gantry 2 or in a case in which the mechanical switch sw2 according to the first modification is turned on.

For this reason, in the third modification, the gantry 2 that has reached the communication range can acquire an eigenvalue (a set value in a radio signal) for each carrying destination in place of sensor information, as in the first and second modifications. That is, the eigenvalue is set in the memory of the gantry control circuitry 28 in place of the sensor information shown in FIG. 13. Hence, when the gantry 2 within the communication range rg2 and the X-ray console 6B can wirelessly communicate with each other, both the gantry 2 and the X-ray console 6B can determine that the gantry 2 has reached the vicinity of the couch 7B of the carrying destination. The remaining communication ranges rg1, rg3, and rg4 function in the same way as described above.

Figure 19:
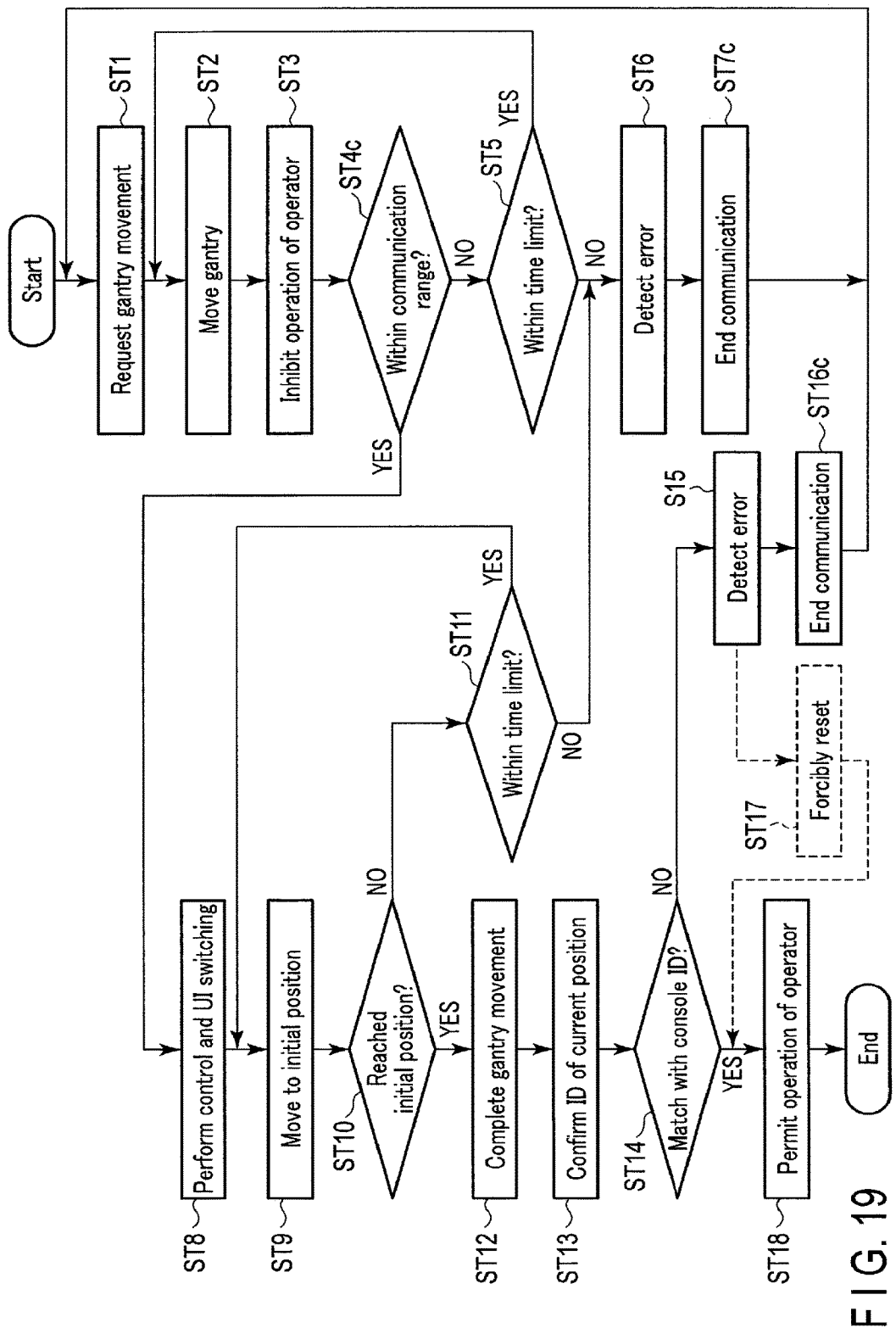
FIG. 19 is a flowchart for explaining the operation according to the third modification of the embodiment.

Hence, for example, as shown in FIG. 19, steps ST1 to ST3, ST5, ST6, ST8 to ST15, ST17, and ST18 irrelevant to the above-described sensors s1_2, S2_3, S3_4, and S4_1 are executed, as described above. Steps ST4, ST7, and ST16 concerning the sensors s1_2, s2_3, s3_4, and s4_1 are executed as shown in steps ST4$c$, ST7$c$, and ST16$c$.

Step ST4$c$ will be described first. Steps ST1 (gantry moving request) to ST3 (inhibition of operations concerning CT examination) are executed. During the carrying of the gantry 2, the gantry control circuitry 28 determines via the wireless communication circuitry 28$b$ whether the gantry has reached the communication range rg2 (step ST4$c$). If NO in step ST4$c$, the processes of steps ST2 to ST5 are repetitively executed within the time limit (YES in step ST5), as described above. Assume that the gantry 2 has reached the communication range rg2 near the couch 7B of the carrying destination. At this time, the wireless communication circuitry 28$b$ in the gantry 2 receives the radio signal transmitted from the X-ray console 6B, thereby wirelessly communicating with the X-ray console 6B. Accordingly, the gantry control circuitry 28 determines, in step ST4$c$ via the wireless communication circuitry 28$b$, that the gantry 2 has reached the communication range of the X-ray console 6B. From then on, the processing from step ST8 is executed in a similar manner.

Step ST7$c$ will be described. If the determination of step ST4$c$ results in NO, and it is outside the time limit (NO in step ST5), an error is detected (step ST6). After that, for example, a radio signal is transmitted from the CT console 3 to notify the gantry 2 of the eigenvalue of the carrying source, the wireless communication is ended (step ST7$c$), and the processing from step ST1 is re-executed.

Step ST16$c$ will be described. If the determination of step ST14 results in NO, an error is detected (step ST15). After that, to reacquire the current position, for example, a radio signal including the eigenvalue of the carrying source is transmitted again from the X-ray console 6B to update the eigenvalue, and the wireless communication is ended (step ST16$c$). After that, the processing from step ST1 is re-executed.

According to the third modification, even if the sensors s1_2, S2_3, S3_4, and S4_1 at the boundaries of the examination rooms and the sensor information of them are omitted, the same effects as in the above-described embodiments and modifications can be obtained by the arrangement that makes the gantry 2 wirelessly communicate with the console of the carrying destination. For easier understanding, a description will be made here with focus on the two examination rooms R1 and R2. For example, when the gantry 2 wirelessly communicates with the first console (3A) or the second console (6B), the control circuitry detects the room (R1 or R2) where the gantry 2 is arranged. Even when such a detection method is used, the control circuitry can control the direction of the tilt movement or the direction of the relative movement in accordance with the room where the gantry 2 is arranged.

The fourth modification will be described next. The fourth modification is directed to appropriately arranging sensors within a range along carrying rails L when carrying the gantry 2 to another couch in the same examination room. For a supplement, in the fourth modification, when another system (couch) exists in the same examination room, which system is connected to the gantry can be recognized based on the positions of sensors. More specifically, the fourth modification corresponds to an arrangement that omits the partition walls and opening/closing doors 9 between the examination rooms in the above embodiments and modifications. According to the fourth modification, even if the gantry 2 is carried to another couch in the same examination room, the same effects as in the above-described embodiments and modifications can be obtained.

According to at least one embodiment described above, a mismatch in UI display and movement control of the gantry can be prevented by an arrangement that switches the moving direction of the gantry or couch top during carrying of the gantry in accordance with the carrying destination of the gantry and the orientation of the gantry after the carrying and switches the display of the moving direction in accordance with the switching control.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray CT system comprising:
a gantry including an X-ray tube, an X-ray detector configured to detect X-rays emitted by the X-ray tube, and an operation interface configured to generate a command signal to command a tilt movement of the gantry in accordance with an operation of an operator;
a first couch arranged in a first room;
a second couch arranged in a second room;
a carrier mechanism including a motor and configured to, when carrying the gantry to the first room, arrange the gantry in an orientation in which a front side of the gantry faces the first couch, and when carrying the gantry to the second room, arrange the gantry in an orientation in which a back side of the gantry faces the second couch; and
control circuitry configured to control a direction of the tilt movement of the gantry in accordance with a room where the gantry is arranged during generation of the command signal by the operation interface.

2. The system according to claim 1, wherein the control circuitry switches, in accordance with the room where the gantry is arranged, at least one display of a positive/negative display of the direction of the tilt movement and a positive/negative display of a moving amount of the tilt movement provided on the operation interface.

3. The system according to claim 1, further comprising
a memory configured to store the room to arrange the gantry and the direction of the tilt movement in association, wherein
the control circuitry controls the direction of the tilt movement based on contents stored in the memory.

4. The system according to claim 1, wherein the control circuitry is arranged in the gantry.

5. The system according to claim 1, further comprising
a gantry detector configured to detect that the gantry is being carried to one of the first room and the second room, wherein
using a detection result of the gantry detector as a trigger, the control circuitry switches the direction of the tilt movement corresponding to the room to which the gantry is carried, and controls the direction of the tilt movement of the gantry based on the switched direction during the generation of the command signal.

6. The system according to claim 1, further comprising:
a first switch arranged near the first couch and configured to switch connection between the gantry arranged in the first room and a first console for the gantry to one of an OFF state and an ON state; and
a second switch arranged near the second couch and configured to switch connection between the gantry arranged in the second room and a second console for the gantry to one of the OFF state and the ON state, wherein
the control circuitry detects the room where the gantry is arranged when the gantry is connected to one of the first console and the second console via a corresponding one of the first switch and the second switch.

7. The system according to claim 1, further comprising:
a first cable arranged in the first room and extended from a first console for the gantry;
a first connector provided at a distal end of the first cable and connectable to the gantry;
a second cable arranged in the second room and extended from a second console for the gantry; and
a second connector provided at a distal end of the second cable and connectable to the gantry, wherein
the control circuitry detects the room where the gantry is arranged when the gantry is connected to one of the first console and the second console via a corresponding one of the first connector and the second connector.

8. The system according to claim 1, further comprising:
0th wireless communication circuitry provided in the gantry;
first wireless communication circuitry provided in a first console arranged in the first room and configured to wirelessly communicating with the 0th wireless communication circuitry; and
second wireless communication circuitry provided in a second console arranged in the second room and capable of wirelessly communicating with the 0th wireless communication circuitry, wherein
the control circuitry detects the room where the gantry is arranged when the gantry wirelessly communicates with one of the first console and the second console.

9. The system according to claim 1, wherein the carrier mechanism carries the gantry in a substantially predetermined orientation.

10. An X-ray CT system comprising:
a gantry including an X-ray tube, an X-ray detector configured to detect X-rays emitted by the X-ray tube, and an operation interface configured to generate a command signal to command a relative movement of the gantry in accordance with an operation of an operator;
a first couch arranged in a first room;
a second couch arranged in a second room;
a carrier mechanism including a motor and configured to, when carrying the gantry to the first room, arrange the gantry in an orientation in which a front side of the gantry faces the first couch, and when carrying the gantry to the second room, arrange the gantry in an orientation in which a back side of the gantry faces the second couch; and
control circuitry configured to control a direction of the relative movement of the gantry and one of the first couch and the second couch in accordance with a room where the gantry is arranged during generation of the command signal by the operation interface.

11. The system according to claim 10, wherein the control circuitry switches, in accordance with the room where the gantry is arranged, at least one display of a positive/negative display of the direction of the relative movement and a positive/negative display of a moving amount of the relative movement provided on the operation interface.

12. The system according to claim 10, further comprising
a memory configured to store the room to arrange the gantry and the direction of the relative movement in association, wherein
the control circuitry controls the direction of the relative movement based on contents stored in the memory.

13. The system according to claim 10, wherein the control circuitry is arranged in the gantry.

14. The system according to claim 10, further comprising
a gantry detector configured to detect that the gantry is being carried to one of the first room and the second room, wherein
using a detection result of the gantry detector as a trigger, the control circuitry switches the direction of the relative movement corresponding to the room to which the gantry is carried, and controls the direction of the relative movement of the gantry based on the switched direction during the generation of the command signal.

15. The system according to claim 10, further comprising:
a first switch arranged near the first couch and configured to switch connection between the gantry arranged in the first room and a first console for the gantry to one of an OFF state and an ON state; and
a second switch arranged near the second couch and configured to switch connection between the gantry arranged in the second room and a second console for the gantry to one of the OFF state and the ON state, wherein
the control circuitry detects the room where the gantry is arranged when the gantry is connected to one of the first console and the second console via a corresponding one of the first switch and the second switch.

16. The system according to claim 10, further comprising:
a first cable arranged in the first room and extended from a first console for the gantry;
a first connector provided at a distal end of the first cable and connectable to the gantry;
a second cable arranged in the second room and extended from a second console for the gantry; and
a second connector provided at a distal end of the second cable and connectable to the gantry, wherein
the control circuitry detects the room where the gantry is arranged when the gantry is connected to one of the first console and the second console via a corresponding one of the first connector and the second connector.

17. The system according to claim 10, further comprising:
0th wireless communication circuitry provided in the gantry;
first wireless communication circuitry provided in a first console arranged in the first room and configured to wirelessly communicating with the 0th wireless communication circuitry; and
second wireless communication circuitry provided in a second console arranged in the second room and configured to wirelessly communicating with the 0th wireless communication circuitry, wherein
the control circuitry detects the room where the gantry is arranged when the gantry wirelessly communicates with one of the first console and the second console.

18. The system according to claim 10, wherein the carrier mechanism carries the gantry in a substantially predetermined orientation.

* * * * *